(12) United States Patent
Matlock et al.

(10) Patent No.: US 10,625,062 B2
(45) Date of Patent: Apr. 21, 2020

(54) DILATION CATHETER ASSEMBLY WITH RAPID CHANGE COMPONENTS

(71) Applicant: Acclarent, Inc., Irvine, CA (US)

(72) Inventors: George L. Matlock, Pleasanton, CA (US); Don Q. Ngo-Chu, Irvine, CA (US); Randy S. Chan, San Jose, CA (US); Jason R. Phillips, Rancho Santa Margarita, CA (US); Tuan Pham, Montclair, CA (US)

(73) Assignee: Acclarent, Inc., Irvine, CA (US)

( * ) Notice: Subject to any disclaimer, the term of this patent is extended or adjusted under 35 U.S.C. 154(b) by 403 days.

(21) Appl. No.: 15/278,588

(22) Filed: Sep. 28, 2016

(65) Prior Publication Data

US 2017/0259048 A1   Sep. 14, 2017

Related U.S. Application Data

(60) Provisional application No. 62/305,083, filed on Mar. 8, 2016.

(51) Int. Cl.
*A61M 29/02* (2006.01)
*A61M 25/09* (2006.01)
(Continued)

(52) U.S. Cl.
CPC ............ *A61M 29/02* (2013.01); *A61B 17/24* (2013.01); *A61M 25/0113* (2013.01);
(Continued)

(58) Field of Classification Search
CPC ............ A61M 29/02; A61M 25/09041; A61M 2029/025; A61M 2210/0681; A61M 2210/0618; A61M 2025/0681; A61M 2025/09125; A61M 29/00; A61M 3/0295; A61M 25/10; A61B 17/24; A61B 2017/00331; A61B 2017/22038; A61B 2017/22049; A61B 2017/00292; A61B 2017/00389
See application file for complete search history.

(56) References Cited

U.S. PATENT DOCUMENTS 7,993,384 B2   8/2011   Wu et al.
9,155,492 B2   10/2015  Jenkins et al.
(Continued)

FOREIGN PATENT DOCUMENTS

WO   WO 2008/049088 A2   4/2008

OTHER PUBLICATIONS

U.S. Appl. No. 62/305,083, filed Mar. 8, 2016.
(Continued)

*Primary Examiner* — Katherine M Shi
(74) *Attorney, Agent, or Firm* — Frost Brown Todd LLC

(57) ABSTRACT

A dilation catheter system includes a body and a shaft assembly. The shaft assembly extends passed a distal end of the body. The shaft assembly includes a fixed guide member, a catheter shaft, a dilator, a removable guide member, and a guidewire. The fixed guide member is fixed relative to the body. The dilator is fixed to the catheter shaft. The catheter shaft is operable to expand the dilator. The removable guide member is operable to selectively attach to the body. The catheter shaft is slidably disposed along the removable guide member such that the catheter shaft is configured to translate along the removable guide member. The guidewire is slidably disposed within the removable guide member.

20 Claims, 32 Drawing Sheets

(51) Int. Cl.
*A61M 25/01* (2006.01)
*A61B 17/24* (2006.01)
*A61B 17/22* (2006.01)
*A61B 17/00* (2006.01)
*A61B 17/29* (2006.01)

(52) U.S. Cl.
CPC .................. *A61M 25/09041* (2013.01); *A61B 2017/00331* (2013.01); *A61B 2017/00389* (2013.01); *A61B 2017/22038* (2013.01); *A61B 2017/22049* (2013.01); *A61B 2017/2929* (2013.01); *A61M 2025/09125* (2013.01); *A61M 2029/025* (2013.01); *A61M 2210/0618* (2013.01); *A61M 2210/0681* (2013.01)

(56) References Cited

U.S. PATENT DOCUMENTS

| | | |
|---|---|---|
| 9,554,817 B2 | 1/2017 | Goldfarb et al. |
| 2005/0197623 A1 | 9/2005 | Leeflang et al. |
| 2008/0243031 A1* | 10/2008 | Seibel .................. A61B 1/0008 600/566 |
| 2010/0030031 A1 | 2/2010 | Goldfarb et al. |
| 2011/0004057 A1 | 1/2011 | Goldfarb et al. |
| 2012/0071727 A1* | 3/2012 | Hanson .................. A61B 17/24 600/249 |
| 2012/0071856 A1* | 3/2012 | Goldfarb ................ A61B 17/24 604/514 |
| 2012/0071857 A1 | 3/2012 | Goldfarb et al. |
| 2013/0261388 A1 | 10/2013 | Jenkins et al. |
| 2013/0303330 A1* | 11/2013 | Stevens ........... A61M 25/09041 475/349 |
| 2014/0074141 A1 | 3/2014 | Johnson et al. |
| 2014/0107427 A1 | 4/2014 | Chow et al. |

OTHER PUBLICATIONS

International Search Report and Written Opinion dated Jun. 13, 2017 for International Application No. PCT/US2017/021304, 21 pages.

* cited by examiner

DILATION CATHETER ASSEMBLY WITH RAPID CHANGE COMPONENTS

PRIORITY

This application claims priority to U.S. Provisional Pat. App. No. 62/305,083, entitled "Dilation Catheter Assembly with Rapid Change Components," filed Mar. 8, 2016, the disclosure of which is incorporated by reference herein.

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guidewire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pub. No. 2011/0004057, entitled "Systems and Methods for Transnasal Dilation of Passageways in the Ear, Nose or Throat," published Jan. 6, 2011, now abandoned, the disclosure of which is incorporated by reference herein. An example of such a system is the Relieva® Spin Balloon Sinuplasty™ System by Acclarent, Inc. of Menlo Park, Calif.

A variable direction view endoscope may be used with such a system to provide visualization within the anatomical passageway (e.g., the ear, nose, throat, paranasal sinuses, etc.) to position the balloon at desired locations. A variable direction view endoscope may enable viewing along a variety of transverse viewing angles without having to flex the shaft of the endoscope within the anatomical passageway. Such an endoscope that may be provided in accordance with the teachings of U.S. Pub. No. 2010/0030031, entitled "Swing Prism Endoscope," published Feb. 4, 2010, now abandoned, the disclosure of which is incorporated by reference herein. An example of such an endoscope is the Acclarent Cyclops™ Multi-Angle Endoscope by Acclarent, Inc. of Menlo Park, Calif.

While a variable direction view endoscope may be used to provide visualization within the anatomical passageway, it may also be desirable to provide additional visual confirmation of the proper positioning of the balloon before inflating the balloon. This may be done using an illuminating guidewire. Such a guidewire may be positioned within the target area and then illuminated, with light projecting from the distal end of the guidewire. This light may illuminate the adjacent tissue (e.g., hypodermis, subdermis, etc.) and thus be visible to the naked eye from outside the patient through transcutaneous illumination. For instance, when the distal end is positioned in the maxillary sinus, the light may be visible through the patient's cheek. Using such external visualization to confirm the position of the guidewire, the balloon may then be advanced distally along the guidewire into position at the dilation site. Such an illuminating guidewire may be provided in accordance with the teachings of U.S. Pub. No. 2012/0078118, entitled "Sinus Illumination Lightwire Device," published Mar. 29, 2012, issued as U.S. Pat. No. 9,155,492 on Oct. 13, 2015, the disclosure of which is incorporated by reference herein. An example of such an illuminating guidewire is the Relieva Luma Sentry™ Sinus Illumination System by Acclarent, Inc. of Menlo Park, Calif.

It may be desirable to provide enhanced control of a guidewire in a dilation catheter system. It may also be desirable to facilitate modular replacement of one or more components of a dilation catheter system. While several dilation catheter systems have been made and used, it is believed that no one prior to the inventors has made or used the invention described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

Figure 1A:
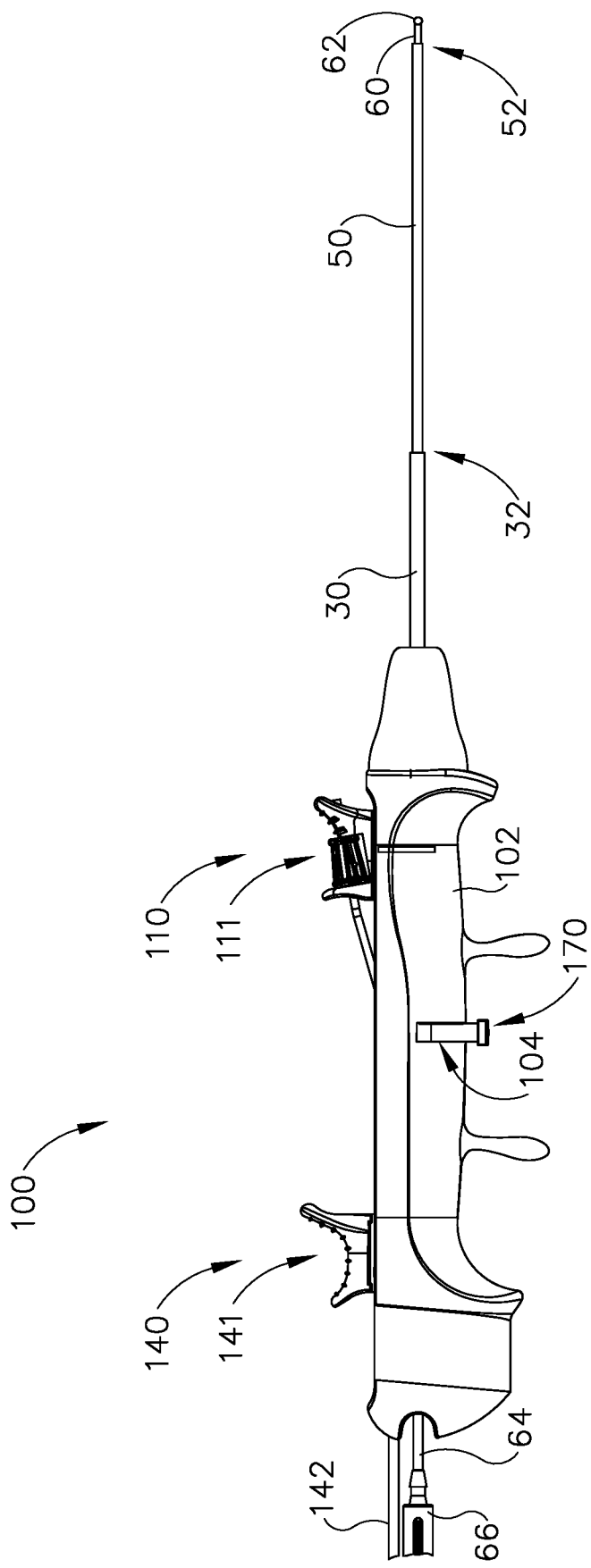
FIG. 1A depicts a side elevational view of an exemplary dilation instrument, in an initial configuration.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Exemplary Dilation Instrument

A. Overview

FIGS. 1A-1D show an exemplary dilation instrument (100) that may be used to dilate the ostium of a paranasal sinus, to dilate some other passageway associated with drainage of a paranasal sinus, or to dilate some other anatomical passageway (e.g., within the ear, nose, or throat, etc.). By way of example only, dilation instrument (100) may be configured and operable in accordance with at least some of the teachings of U.S. Pub. No. 2012/0071857, entitled "Methods and Apparatus for Treating Disorders of the Sinuses," published Mar. 22, 2012, now abandoned, the disclosure of which is incorporated by reference herein. In addition, or in the alternative, dilation instrument (100) may be configured and operable like the Relieva Scout® Sinus Dilation System by Acclarent, Inc. of Menlo Park, Calif.

Dilation instrument (100) of the present example comprises a handle assembly (102), a fixed guide member (30), a removable guide member (50), a guidewire movement assembly (110), a dilation catheter movement assembly (140), and a guide member attachment assembly (170). Handle assembly (102) is configured to be gripped by a single hand of an operator. Fixed guide member (30) extends distally from handle assembly (102) and is substantially straight. In some versions, fixed guide member (30) is formed of metal, though any other suitable material(s) may be used. In the present example, the longitudinal position and angular position of fixed guide member (30) is fixed relative to handle assembly (102).

Figure 1B:
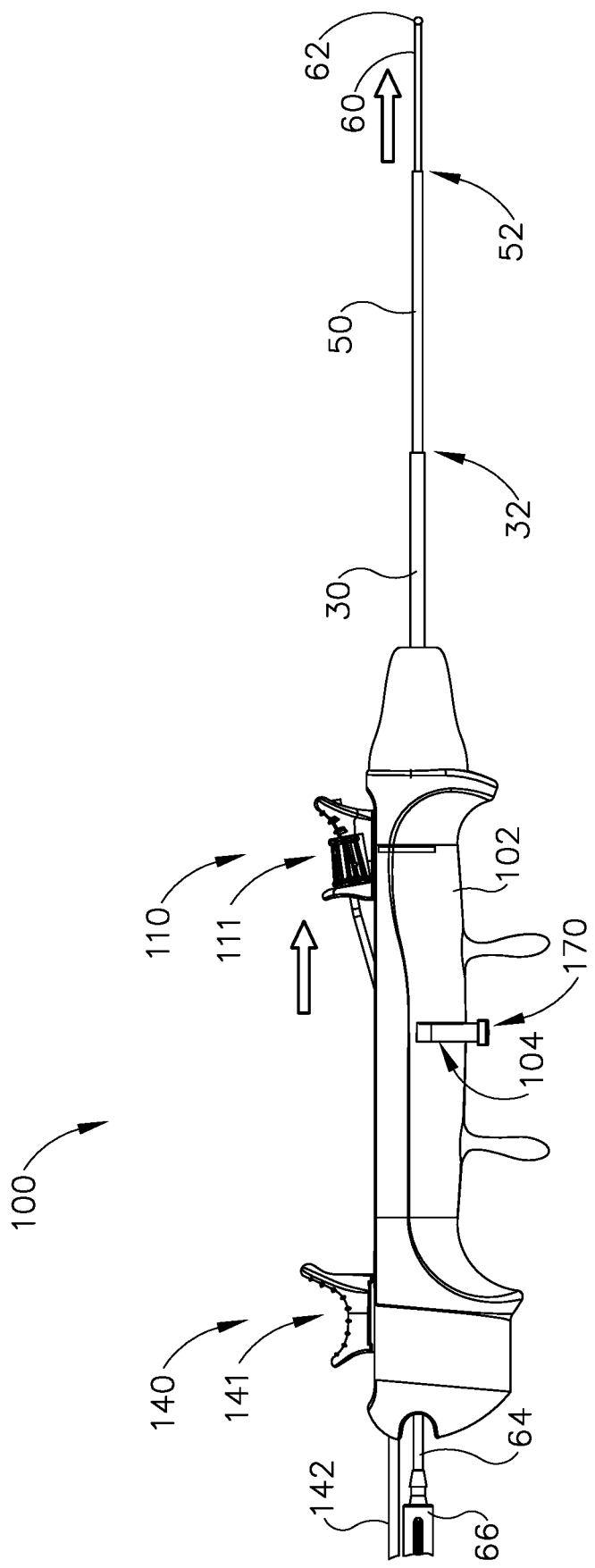
FIG. 1B depicts a side elevational view of the dilation instrument of FIG. 1A, with a guidewire advanced to a distal position.
Figure 1C:
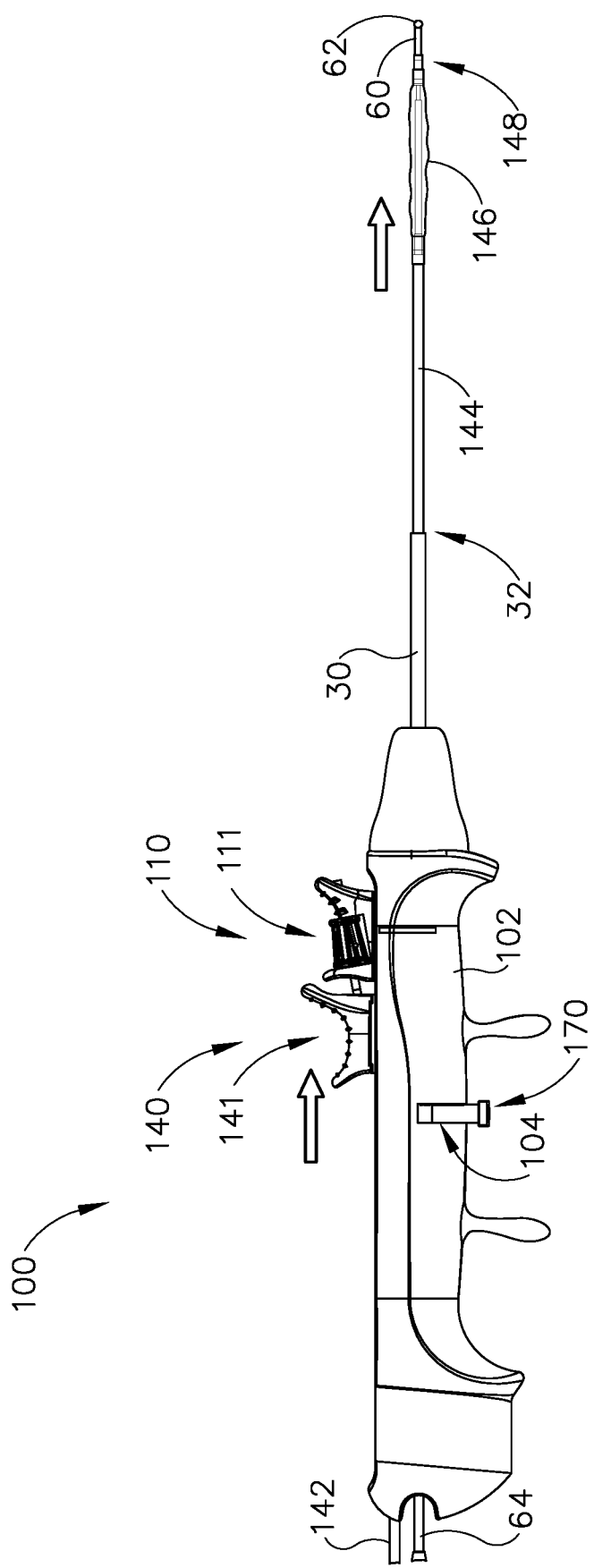
FIG. 1C depicts a side elevational view of the dilation instrument of FIG. 1A, with a dilation catheter advanced to a distal position, where the dilation catheter is in a deflated state.
Figure 2A:
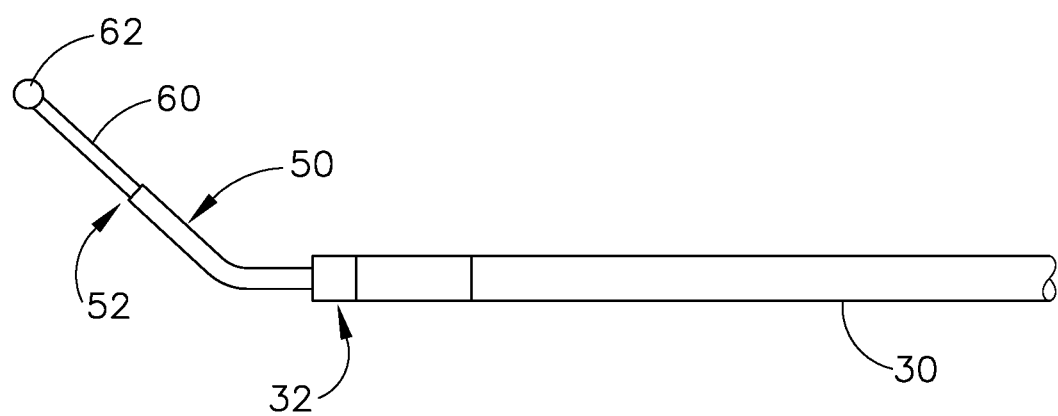
FIG. 2A depicts a side elevational view of the distal end of the dilation instrument of FIG. 1A, with the guidewire advanced to the distal position.

Removable guide member (50) protrudes distally from the open distal end (32) of fixed guide member (30). The outer diameter of removable guide member (50) is smaller than the inner diameter of fixed guide member (30), such that a cylindraceous gap is defined between the outer diameter of removable guide member (50) and the inner diameter of fixed guide member (30). This cylindraceous gap is sized to accommodate a translating catheter shaft (144) as will be described in greater detail below. In other words, catheter shaft (144) may be slidably disposed over removable guide member (50). Catheter shaft (144) is connected to a dilator (146) at a distal end. While removable guide member (50) is shown as having a straight configuration in FIGS. 1A-1C, removable guide member (50) may have a rigid, preformed bend. FIG. 2A shows one merely illustrative example of a form that a preformed bend may take. It should be understood that various bend angles may be selected from based on the target anatomy (e.g., maxillary sinus ostium, frontal recess, sphenoid sinus ostium, Eustachian tube, etc.). In the present example, removable guide member (50) is formed of rigid metal, though any other suitable material(s) may be used. As will be described in greater detail below, removable guide member (50) may be inserted within fixed guide member (30) and catheter shaft (144), then removable guide member (50) may be selectively fixed relative to body assembly (102) via guide member attachment assembly (170).

Guidewire (60) is slidably received in a central lumen defined in removable guide member (50). Guidewire (60) includes a rounded tip feature (62) that is located distal to the open distal end (52) of removable guide member (50). Guidewire (60) is secured to a guidewire movement assembly (110), which is slidably coupled with handle assembly (102). Guidewire movement assembly (110) is thus operable to slide guidewire (60) between a proximal position (FIG. 1A) and a distal position (FIG. 1B). In the present example, tip feature (62) has an outer diameter that is larger than the inner diameter of distal end (52) of removable guide member (50), such that tip feature (62) cannot be retracted proximally back through removable guide member (50). In some versions, guidewire (60) includes one or more optical fibers, and tip feature (62) is configured to emit light communicated through such optical fibers. This may enable an operator to verify positioning of tip feature (62) within a sinus cavity through a transillumination effect as is known in the art. The proximal end of guidewire (60) may be coupled with a suitable light source. By way of example only, guidewire (60) may be configured and operable in accordance with at least some of the teachings of U.S. Pub. No. 2012/0078118, issued as U.S. Pat. No. 9,155,492 on Oct. 13, 2015, the disclosure of which is incorporated by reference herein. In addition, or in the alternative, guidewire (60) may be configured and operable like the Relieva Luma Sentry® Sinus Illumination System by Acclarent, Inc. of Menlo Park, Calif. Other suitable forms that guidewire (60) may take will be apparent to those of ordinary skill in the art in view of the teachings herein.

Figure 2B:
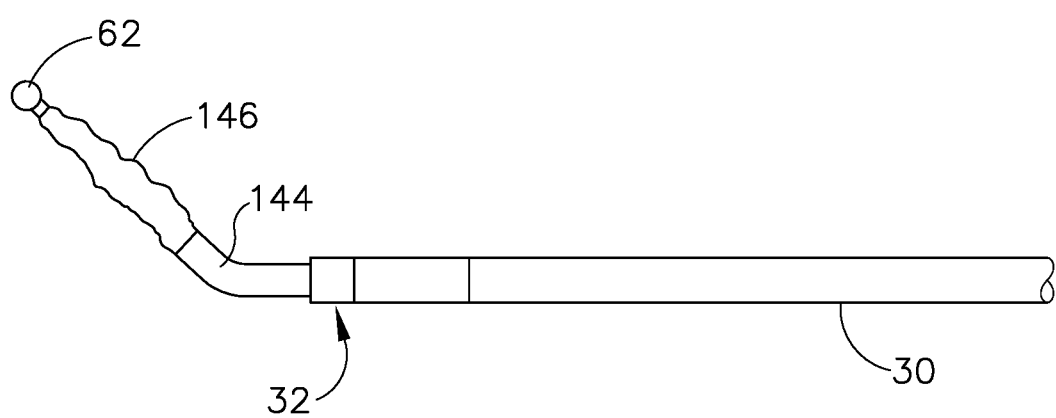
FIG. 2B depicts a side elevational view of the distal end of the dilation instrument of FIG. 1A, with the dilation catheter advanced to the distal position.
Figure 2C:
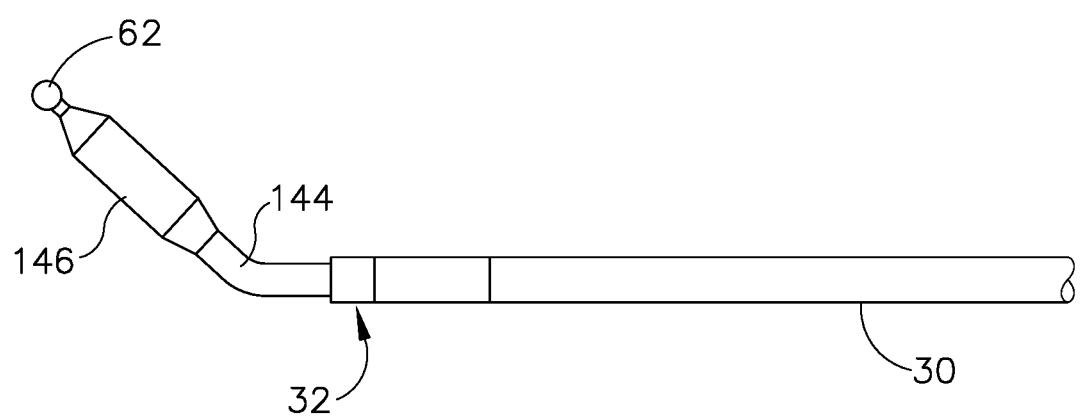
FIG. 2C depicts a side elevational view of the distal end of the dilation instrument of FIG. 1A, with the dilator of the dilation catheter in an expanded state.
Figure 3:
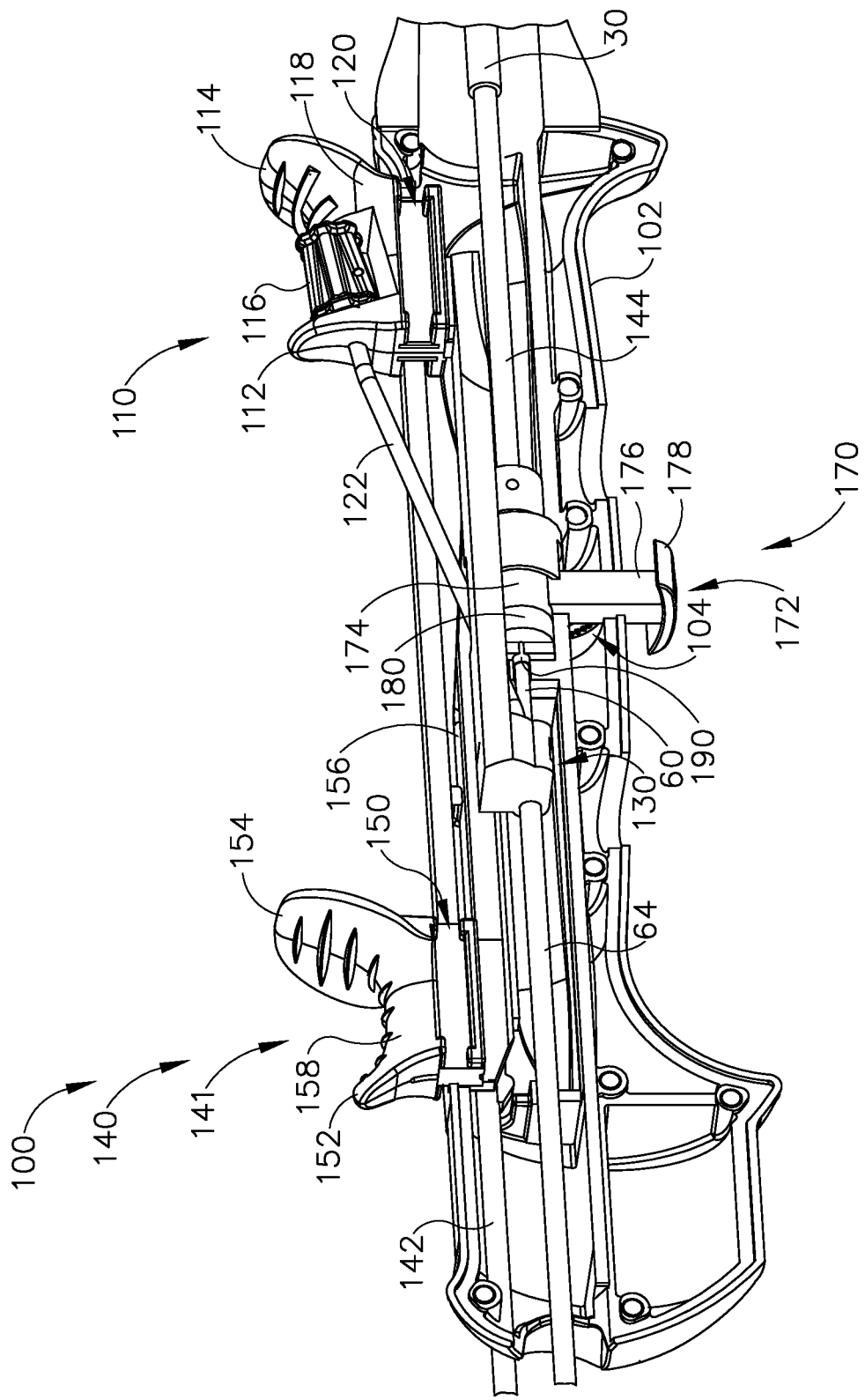
FIG. 3 depicts a perspective view of the dilation instrument of FIG. 1A with half of the body removed to reveal internal components.
Figure 4:
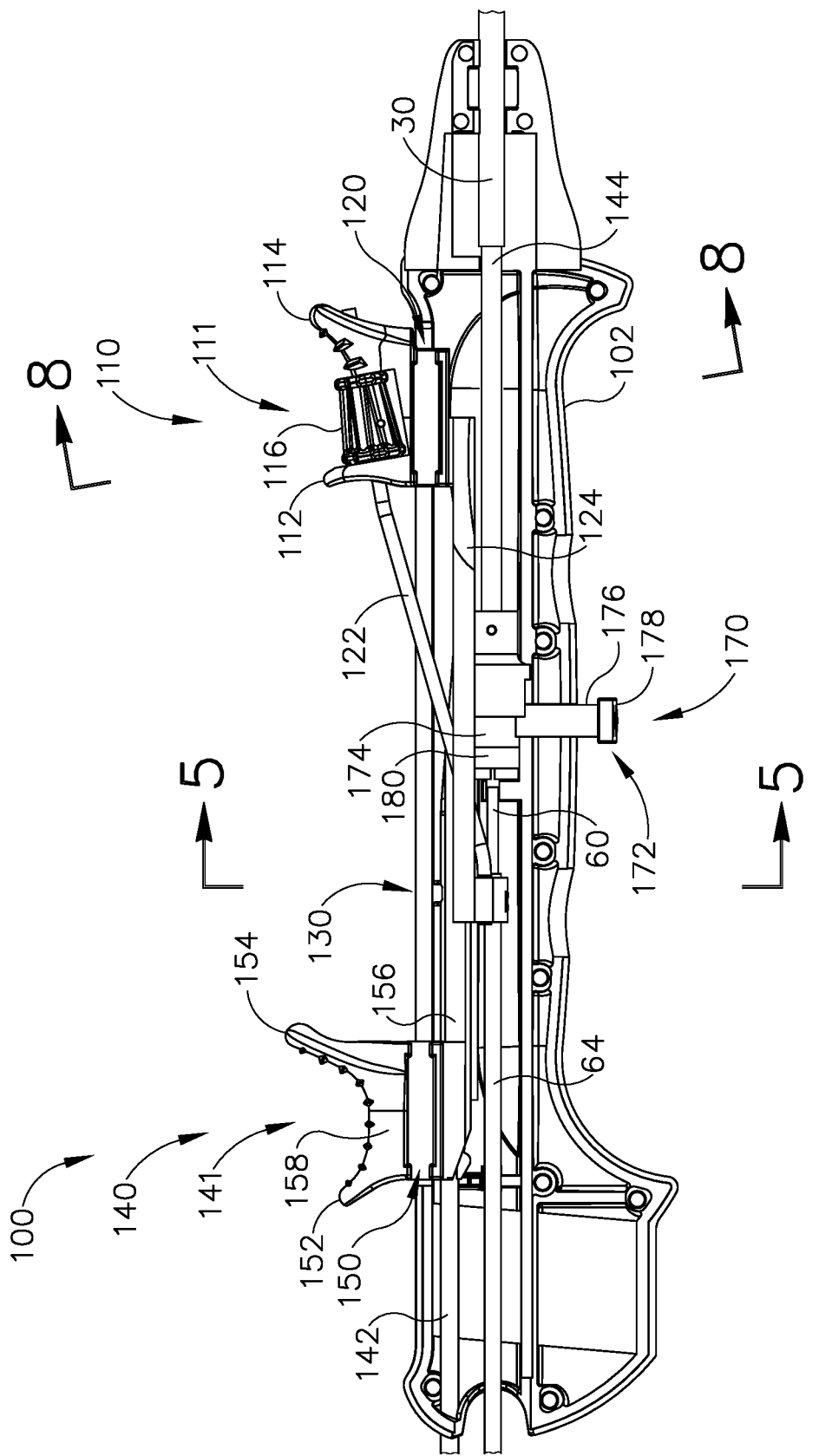
FIG. 4 depicts a side elevational view of the dilation instrument of FIG. 1A with half of the body removed to reveal internal components.

Catheter shaft (144) is slidably disposed along removable guide member (50) and is thus operable to translate through the cylindraceous gap as defined between the outer diameter of removable guide member (50) and the inner diameter of fixed guide member (30). Catheter shaft (144) is secured to a dilation catheter movement assembly (140), which is slidably coupled with handle assembly (102). Catheter movement assembly (140) is thus operable to slide catheter shaft (144) between a proximal position (FIGS. 1B and 2A) and a distal position (FIGS. 1C and 2B). Due to the rigid nature of removable guide member (50), catheter shaft (144) may conform to the longitudinal profile of removable guide member (50), as shown in FIGS. 2B-2C.

Catheter movement assembly (140) includes a grip (158), an inflation shaft (142) secured to grip (158), and an elongate body (156) unitarily connected to both grip (141) and catheter shaft (144). Grip (158) includes a cantle (152), a pommel (154) and a body (158). Body (158) defines a pair of slots (150) that slidably attach dilation catheter movement assembly (140) to handle assembly (102). Of course, dilation catheter movement assembly (140) may be coupled with handle assembly (102) in any other suitable fashion. Pommel (154) and cantle (152) allow a user to slide catheter movement assembly (140) with a finger. Therefore, a user may slide grip (158) relative to handle assembly (102), which also slides inflation shaft (142), elongate body (156), catheter shaft (144), and dilator (146).

Figure 6:
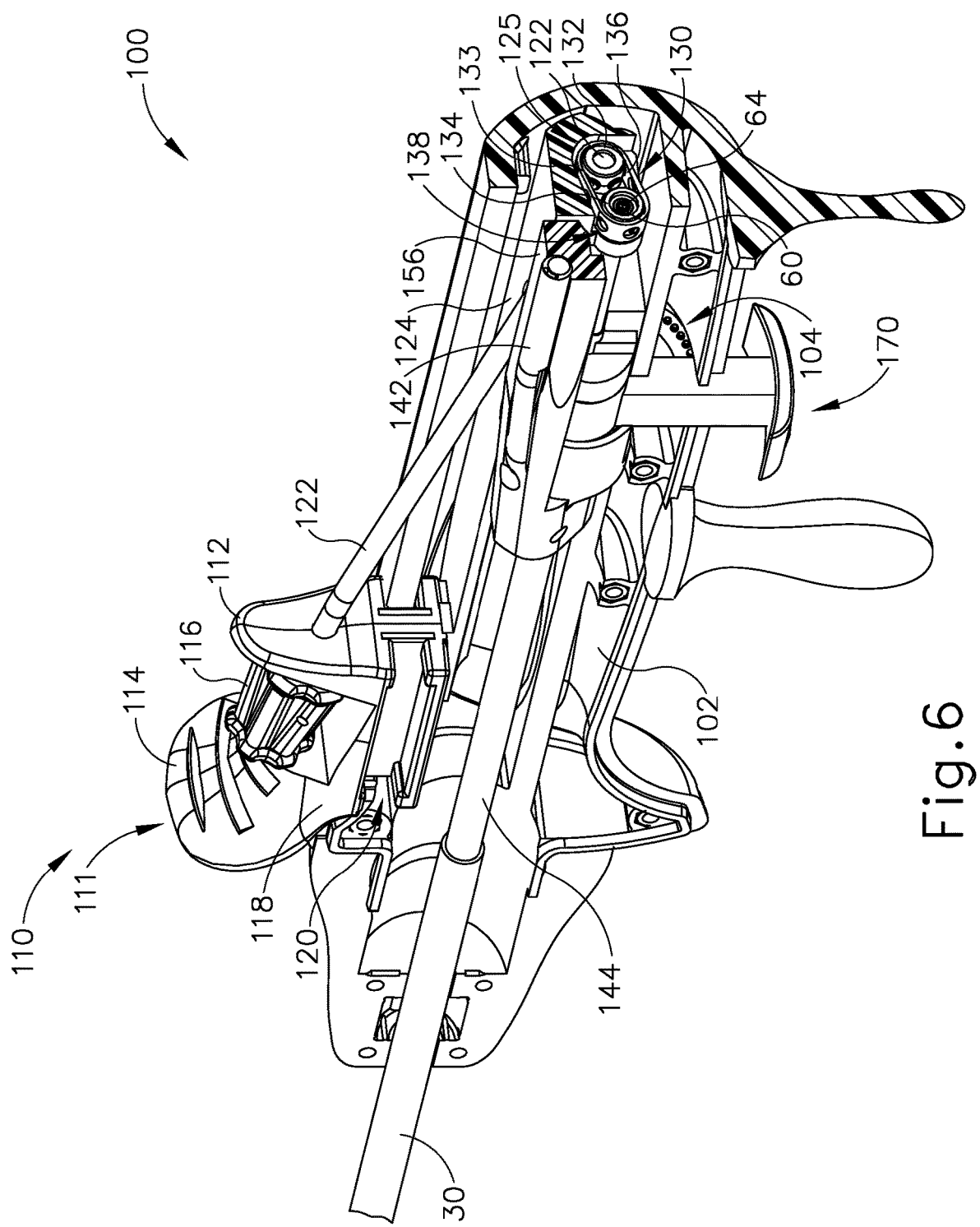
FIG. 6 depicts a cross-sectional perspective view of the guidewire movement assembly of FIG. 5 in combination with other components of the dilation instrument of FIG. 1A, taken along line 5-5 of FIG. 4.
Figure 7:
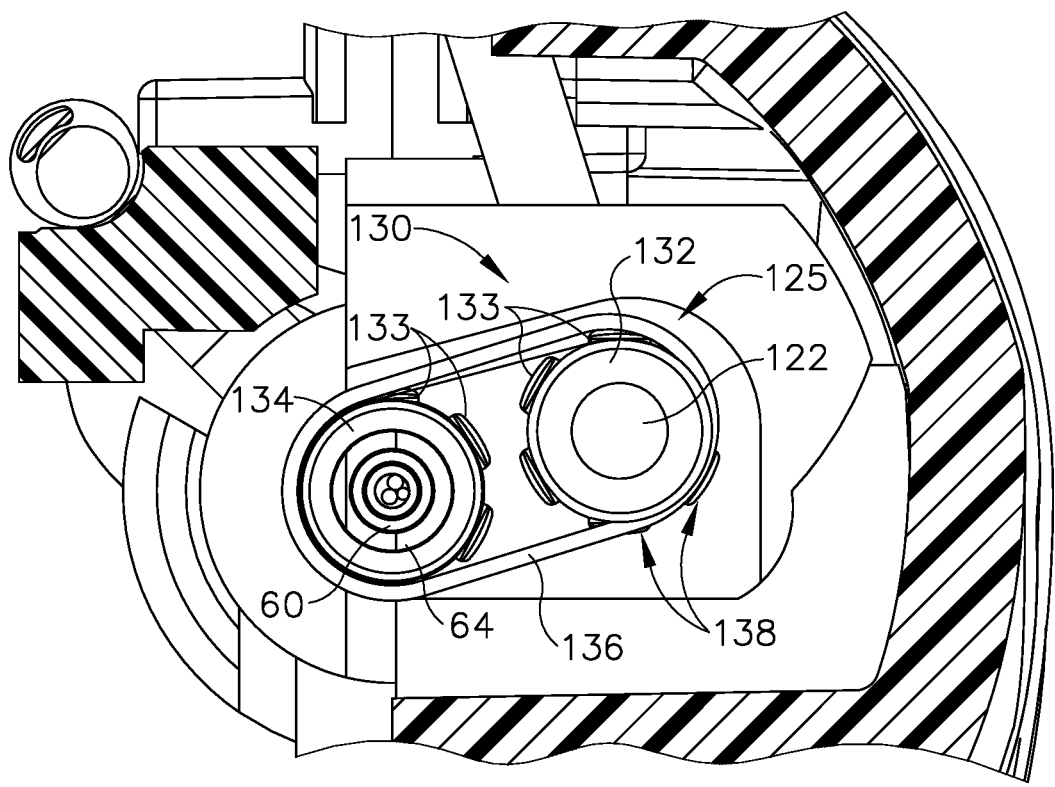
FIG. 7 depicts an enlarged cross-sectional end view of the guidewire movement assembly of FIG. 5, taken along line 5-5 of FIG. 4.
Figure 8:
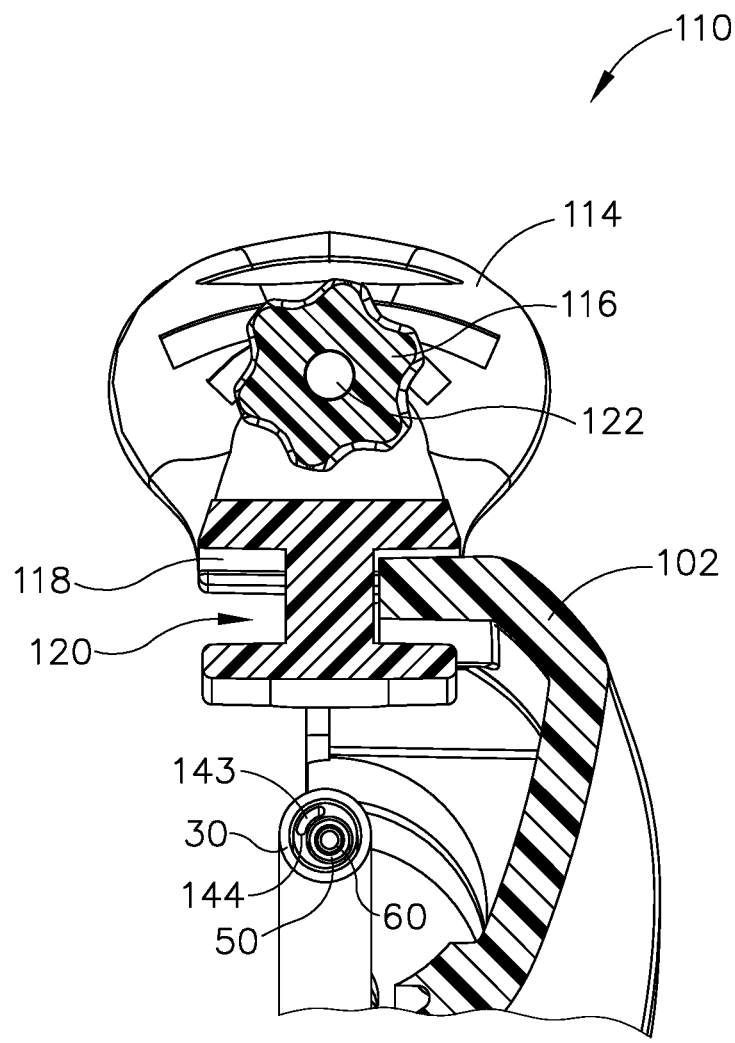
FIG. 8 depicts a cross-sectional view of the guidewire movement assembly of FIG. 5, taken along line 8-8 of FIG. 4.
Figure 9:
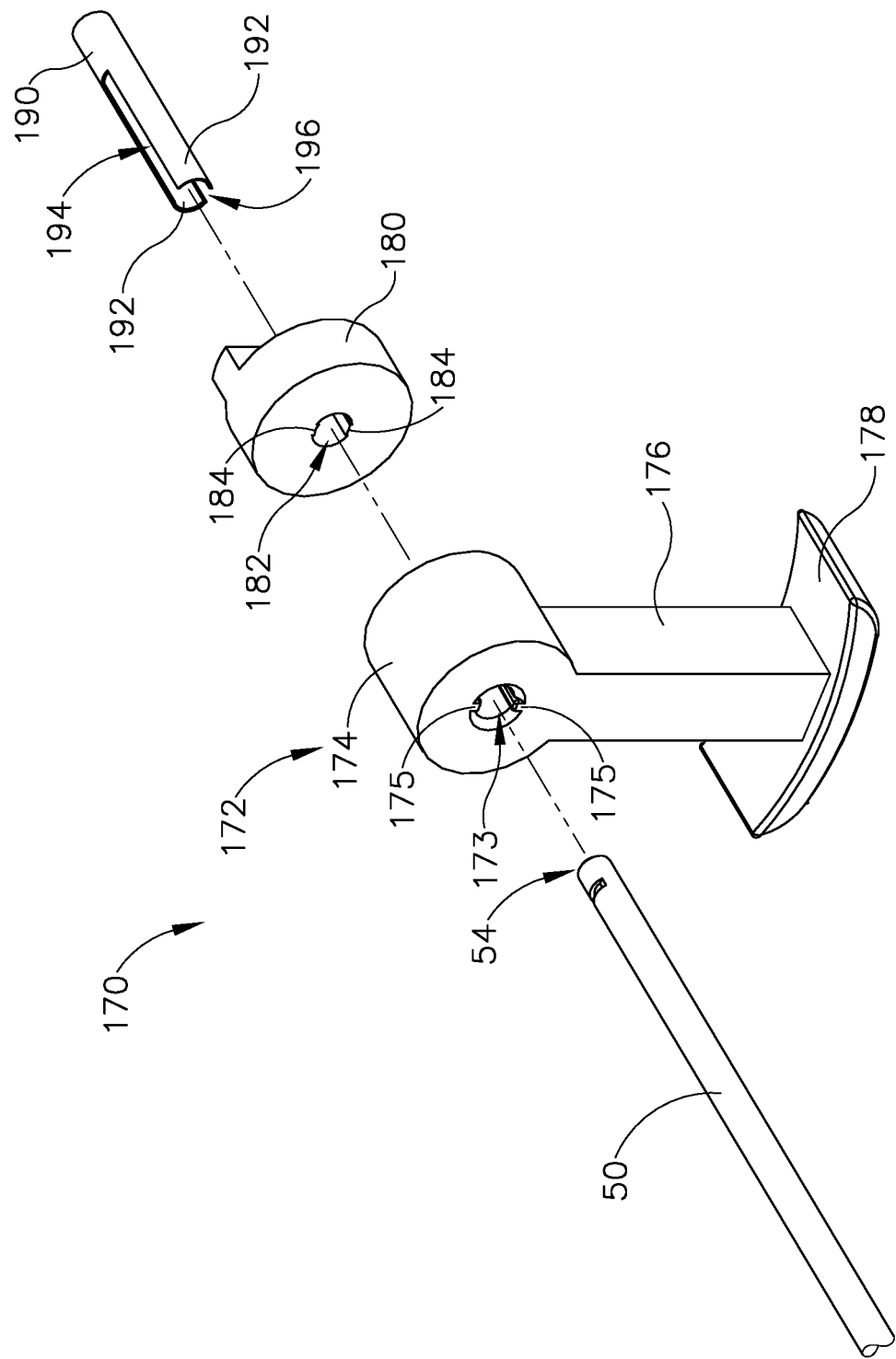
FIG. 9 depicts an exploded perspective view of a guide member attachment assembly of the dilation instrument of FIG. 1A.

As best seen in FIGS. 6 and 8, inflation shaft (142) is in fluid communication with both elongate body (156) and catheter shaft (144) via inflation lumen (143). Inflation lumen (143) extends from inflation shaft (142), through elongate body (156) and catheter shaft (144) all the way to dilator (146). Therefore, inflation lumen (143) is capable of providing fluid to dilator (146) and extracting fluid from dilator (146) in order to inflate and deflate dilator (146). Inflation shaft (142) may be fluidly connected to a fluid source in order to inflate and deflate dilator (146) with any suitable connections known in the art in view of the teachings herein.

When catheter shaft (144) translates from the proximal position to the distal position, catheter shaft (144) and dilator (146) pass over the open distal end (52) of removable guide member (50) and then traverse along at least a portion of the length of guidewire (60) that extends distally from open distal end (52) of removable guide member (50). In some versions, dilation instrument (100) is configured such that catheter shaft (144) is unable to translate distally to a position where the distal end of catheter shaft (144) is distal to tip feature (62) of guidewire (60). For instance, guidewire movement assembly (110) may engage dilation catheter movement assembly (140)) when catheter shaft (144) is driven to a distal-most position, and this engagement between guidewire movement assembly (110) and dilation catheter movement assembly (140) may prevent the distal end of catheter shaft (144) from engaging or otherwise passing distally over tip feature (62) of guidewire (60). This engagement may also enable guidewire movement assembly (110) to be used to advance a proximally positioned guidewire (60) and catheter shaft (144) distally simultaneously, since guidewire movement assembly (110) would drive a proximally positioned dilation catheter movement assembly (140) distally. Thus, instrument (100) need not necessarily be operated in a manner where guidewire (60) is advanced distally, as a discrete act in a sequence, before catheter shaft (144) is advanced distally.

Figure 1D:
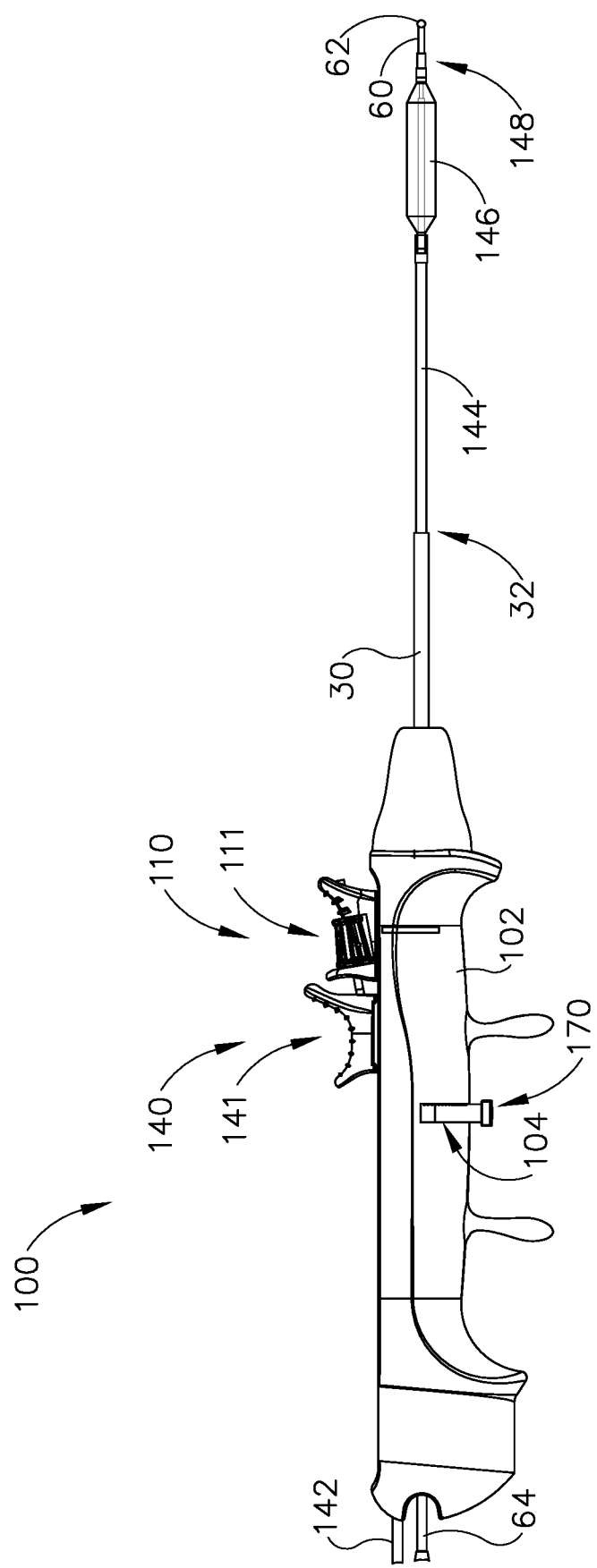
FIG. 1D depicts a side elevational view of the dilation instrument of FIG. 1A, with the dilation catheter advanced to the distal portion, where the dilation catheter is in an inflated state.

As mentioned above, the distal end of catheter shaft (144) is attached to dilator (146). Dilator (146) is operable to transition between a non-expanded state (FIGS. 1C and 2B) and an expanded state (FIGS. 1D and 2C). In the non-expanded state, dilator (146) may be inserted into a sinus ostium or another drainage passageway associated with a paranasal sinus. Dilator (146) may then be expanded to dilate the sinus ostium or other drainage passageway as described in various references herein. In the present example, dilator (146) comprises an inflatable balloon that receives saline (or some other fluid) for inflation, though it should be understood that dilator (146) may instead take a variety of other forms. In some versions, catheter shaft (144) is fluidly coupled with an inflator instrument that is constructed and operable in accordance with at least some of the teachings of U.S. Pub. No. 2014/0074141, entitled "Inflator for Dilation of Anatomical Passageway," published Mar. 13, 2014, issued as U.S. Pat. No. 9,962,530 on May 8, 2018, the disclosure of which is incorporated by reference herein.

B. Exemplary Guidewire Movement Assembly

FIGS. 3-8 show guidewire movement assembly (110) engaging guidewire (60) at the longitudinal axis that is shared by catheter shaft (144), removable guide member (50), and guidewire (60); while providing a control feature that may be engaged by the operator at a location that is offset from the longitudinal axis that is shared by catheter shaft (144), removable guide member (50), and guidewire (60). Guidewire movement assembly (110) further includes a rotary member (116) that is operable to rotate guidewire (60) about the longitudinal axis of guidewire (60).

Guidewire movement assembly (110) of the present example includes a grip (111) unitarily connected to an elongate body (124), a rotary shaft (122), and a gearbox (130) attached to elongate body (124). Elongate body (124) has sufficient rigidity to provide unitary translation of guidewire movement assembly (110). Elongate body (124) extends from grip (111) to gearbox (130). Grip (111) includes a cantle (112), a pommel (114), a body (118), and rotary member (116). Body (118) defines a pair of slots (120) that slidably attach guidewire movement assembly (110) to handle assembly (102). Of course, guidewire movement assembly (110) may be coupled with handle assembly (102) in any other suitable fashion. Pommel (114) and cantle (112) allow a user to slide guidewire movement assembly (110) with a finger. Therefore, a user may unitarily slide guidewire movement assembly (110) relative to handle assembly (102).

Rotary member (116) is rotatably received between cantle (112) and pommel (114). Rotary member (116) is thus rotatable relative to body (118) and is exposed for direct contact and engagement by an operator's finger. Rotary shaft (122) extends between rotary member (116) and gear box (130). Gear box (130) is located at the proximal end of rotary shaft (122) and is secured to guidewire (66) such that guidewire (66) translates longitudinally with guidewire movement assembly (110). However, gear box (130) also permits guidewire (60) to rotate within gear box (130), as will be described in greater detail below.

Figure 5:
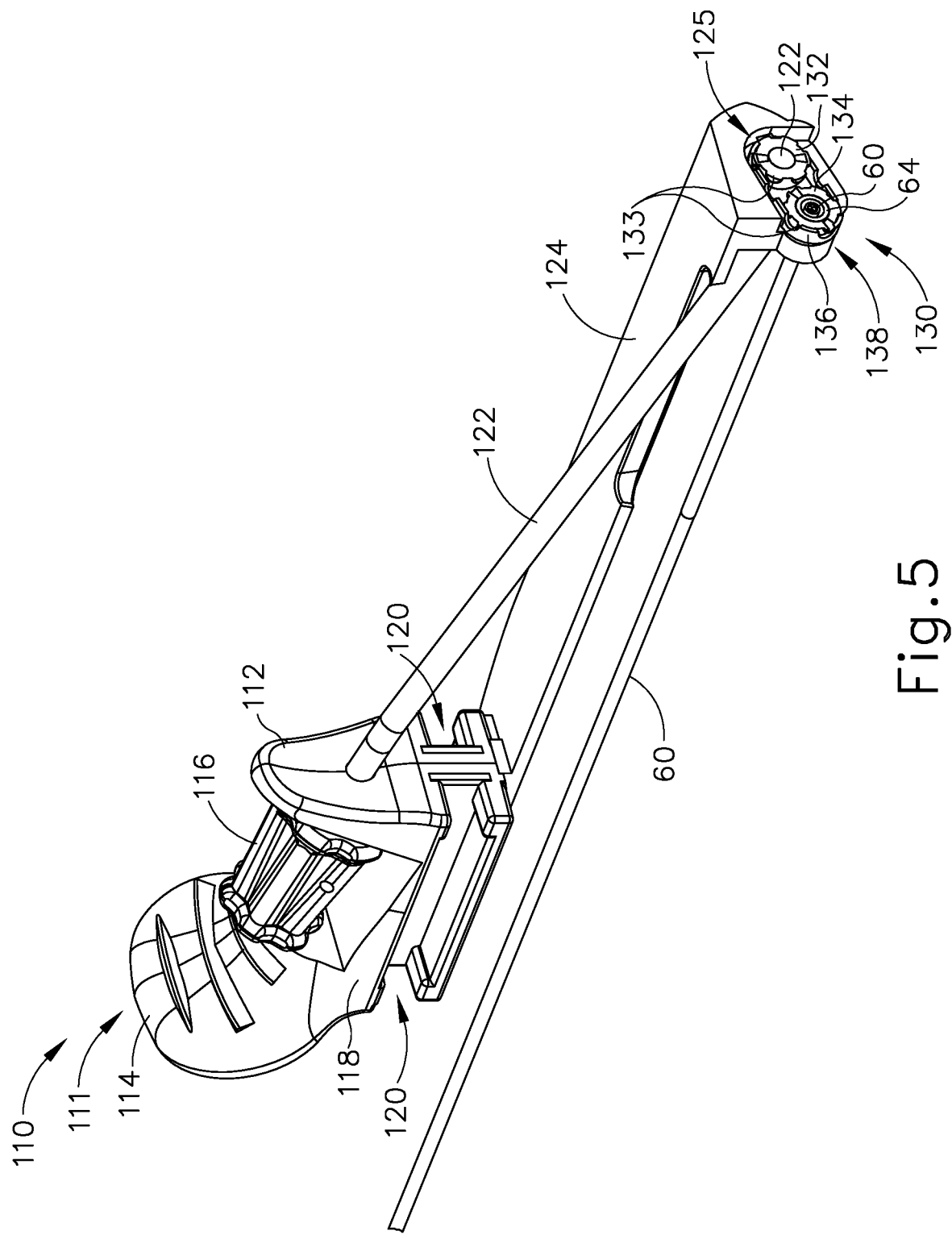
FIG. 5 depicts a cross-sectional perspective view of a guidewire movement assembly of the dilation instrument of FIG. 1A, taken along line 5-5 of FIG. 4.

As best seen in FIGS. 5-6 the proximal end of elongate body (124) defines a recess (125) that houses gearbox (130). Gearbox (130) includes a first control wheel (132), a second control wheel (134), and a belt (136). First control wheel (132) is unitarily connected to rotary shaft (122). Therefore, rotations of rotary member (116) may rotate rotary shaft (122) and first control wheel (132) unitarily. Second control wheel (134) is unitarily connected to a shrink tubing attachment (64). Shrink tubing attachment (64) is unitarily connected to guidewire (60). Therefore, rotation of second control wheel (134) may also rotate guidewire (60) unitarily about the longitudinal axis of guidewire (60).

First control wheel (132) and second control wheel (134) each include a plurality of protrusions (133), while belt (136) defines a plurality of holes (138). Holes (138) are dimensioned to mate with protrusions (133) such that movement of belt (136) may rotate control wheels (132, 134). Therefore, a user may spin rotary member (116), which in turn rotates rotary shaft (122). Rotary shaft (122) then rotates first control wheel (132). First control wheel (132) drives belt (136) due to interaction between protrusions (133) and holes (138). Belt (136) then drives second control wheel (134) through interaction between protrusions (133) and holes (138), which in turn rotates shrink tubing attachment (64) and guidewire (60). In other words, a user may rotate guidewire (60), about the longitudinal axis defined by guidewire (60), by spinning rotary member (116).

While belt (136) and protrusions (133) are used to transfer rotation of first control wheel (132) to second control wheel (134), it should be understood that any other suitable devices may be utilized as would be apparent to one having ordinary skill in the art in view of the teachings herein. For instance, a pulley, sheave, or gears may be used in replace of control wheels (132, 134). Additionally, a friction flat belt, a toothed belt, or a chain may be used in place of belt (136).

Because of the position of gear box (130) in this example, guidewire (60) is able to pass through handle assembly (102) in a substantially straight manner, along the same longitudinal axis that is shared by removable guide (50), catheter shaft (144), and guidewire (60). Second control wheel (132) is centered on this longitudinal axis. It should be understood that the positioning of second control wheel (132) on this longitudinal axis may provide the operator with more sensitive tactile feedback as the operator drives rotation of guidewire (60) via rotary member (116).

FIGS. 20-23 show an alternative guidewire movement assembly (310) that may be readily incorporated into dilation instrument (100) in place of guidewire movement assembly (110) described above. It should therefore be understood that guidewire movement assembly (310) may be slidably coupled with handle assembly (102). Similar to guidewire movement assembly (110) described above, guidewire movement assembly (310) may engage guidewire (60) at the longitudinal axis shared by catheter shaft (144), removable guide member (50), and guidewire (60); while providing a control feature that may be engaged by the operator at a location that is offset from the shared longitudinal axis. Additionally, guidewire (60) may be secured to guidewire movement assembly (310) such that movement of guidewire movement assembly (310) relative to handle assembly (102) also drives guidewire (60) relative to handle assembly (102). In other words, guidewire movement assembly (310) is operable to slide guidewire (60) between the proximal position (FIG. 1A) and the distal position (FIG. 1B).

Guidewire movement assembly (310) of the present example includes an elongate body (324), a distal housing (312), a rotating member (316), and a rotational transfer assembly (330). As will be described in greater detail below rotating members (316) may rotate relative to elongate body (324) in order to drive rotational transfer assembly (330), which in turn may rotate guidewire (60) about its own longitudinal axis.

Distal housing (312) may receive longitudinal portions of guidewire (360), catheter shaft (144), and/or removable guide member (50). Distal housing (312) may also be slidably coupled with selected portions of handle assembly (102) for stabilizing guidewire movement assembly (310) relative to handle assembly (102). However, distal housing (312) is entirely optional. Therefore, distal housing (312) may be omitted entirely from some versions.

Figure 20:
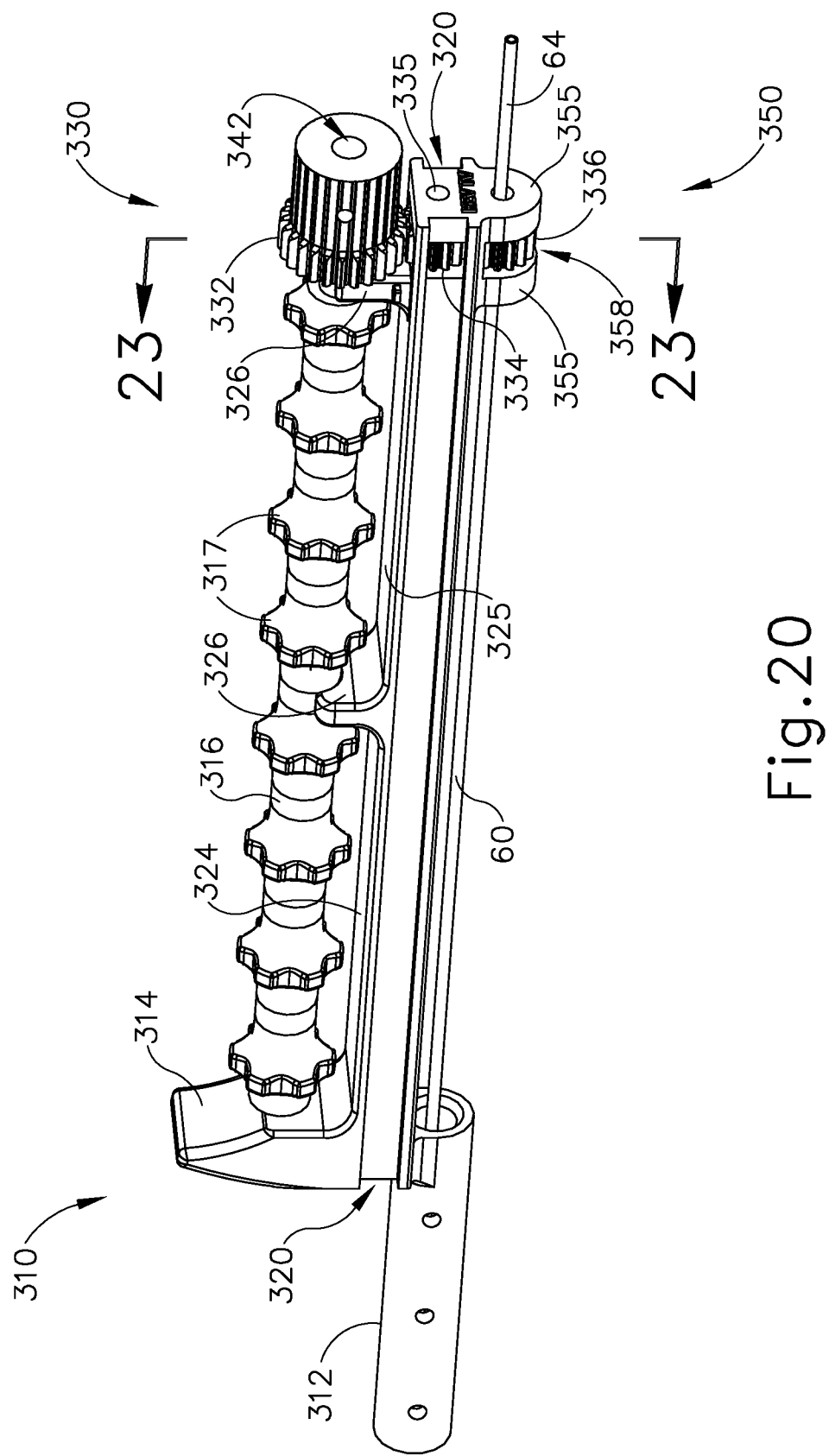
FIG. 20 depicts a perspective view of an alternative guidewire movement assembly that may be readily incorporated into the dilation instrument of FIG. 1A in replacement of the guidewire movement assembly of FIG. 1A.

As best seen in FIG. 20, elongate body (324) extends between proximal housing (312) and rotational transfer assembly (330). Elongate body (324) defines a pair of slots (320) that may be used to slidably couple guidewire movement assembly (310) to handle assembly (102). Elongate body (324) includes a top surface (325), a pommel (314) extending from top surface (325), and a pair of rotary supports (326) extending from top surface (325).

A plurality of rotating grips (317) extend radially outwardly from rotating member (316). Rotating member (316) is rotatably attached to pommel (314) such that rotating member (316) may not translate relative to elongate body (324); but such that rotating member (316) may rotate about its own longitudinal axis relative to elongate body (324). Therefore, an operator may engage a portion of rotating grips (317) with one or more fingers in order to rotate rotating member (316) about its own longitudinal axis. Additionally, or alternatively, an operator may translate guidewire movement assembly (310) and guidewire (60) relative to handle assembly (102). Rotating member (316) may be rotatably attached to pommel (314) by any suitable means as will be apparent to one having ordinary skill in the art in view of the teachings herein.

Figure 21:
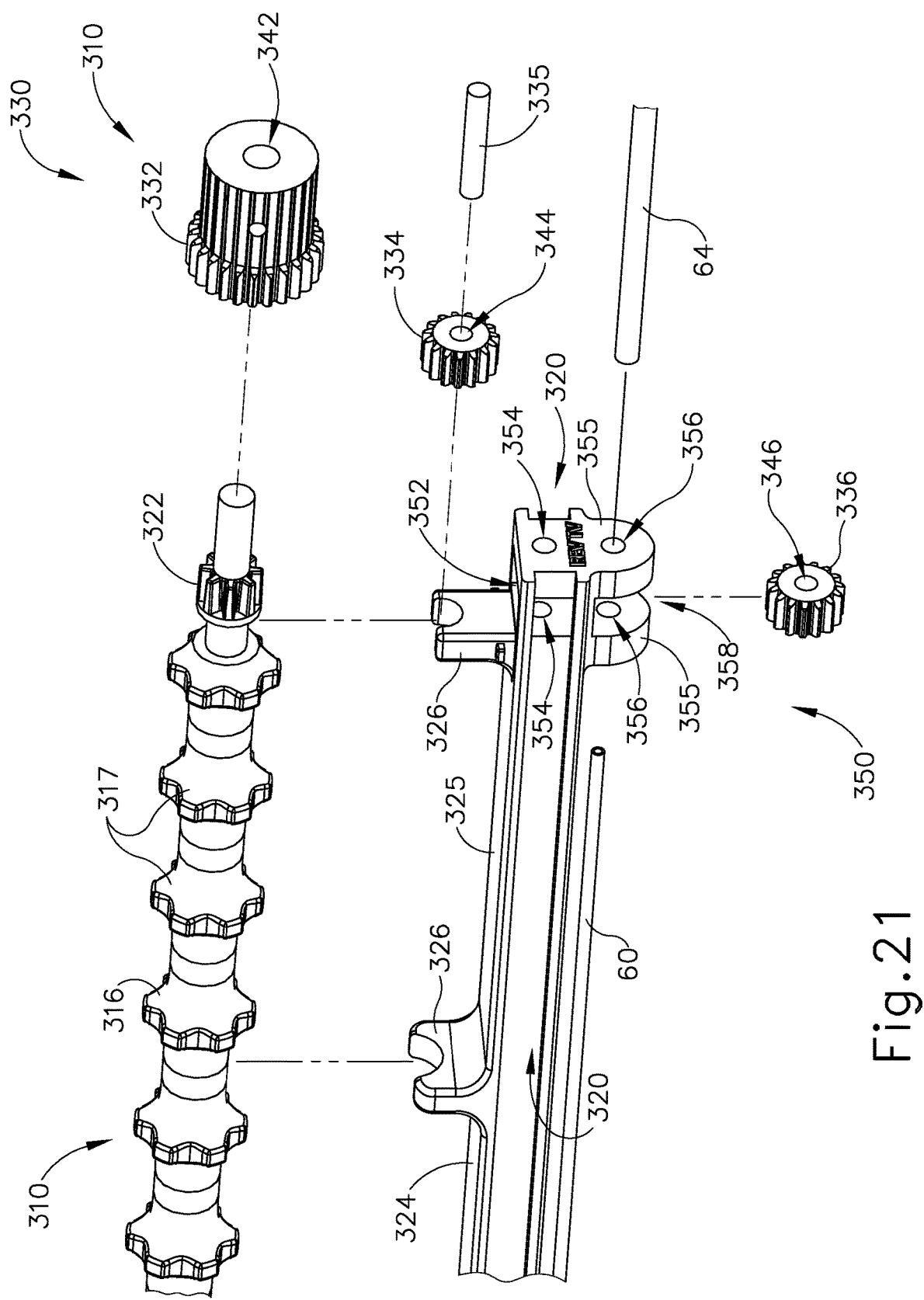
FIG. 21 depicts an exploded perspective view the guidewire movement assembly of FIG. 20.

As best seen in FIG. 21, rotating member (316) includes a gear coupling member (322). As will be described in greater detail below, gear coupling member (322) is dimensioned to unitarily couple with a selected portion of rotational transfer assembly (330) in order to convert rotation of rotating member (316) about its respective longitudinal axis into rotation of guidewire (60) about its respective longitudinal axis.

Rotary supports (326) are dimensioned to vertically and laterally support rotating member (316) such that as rotating member (316) is rotating about its own longitudinal axis, rotating member (316) does not laterally or vertically deflect/translate relative to elongate body (324).

Rotational transfer assembly (330) includes a primary gear (332), an idler gear (334), a secondary gear (336), and a gear housing (350). Gear housing (350) is unitarily attached to elongate body (324). In the current example, gear housing (350) is located at a proximal end of elongate body (324). However, gear housing (350) may be located at any other suitable location as would be apparent to one having ordinary skill in the art in view of the teachings here. Gear housing (350) comprises a pair of housing members (355), which are longitudinally spaced apart to define a cavity (358), and an opening (352) extending from top surface (325) toward cavity (358). Additionally, each housing member (355) defines an aligned pin hole (354) and an aligned guidewire hole (356).

Figure 22:
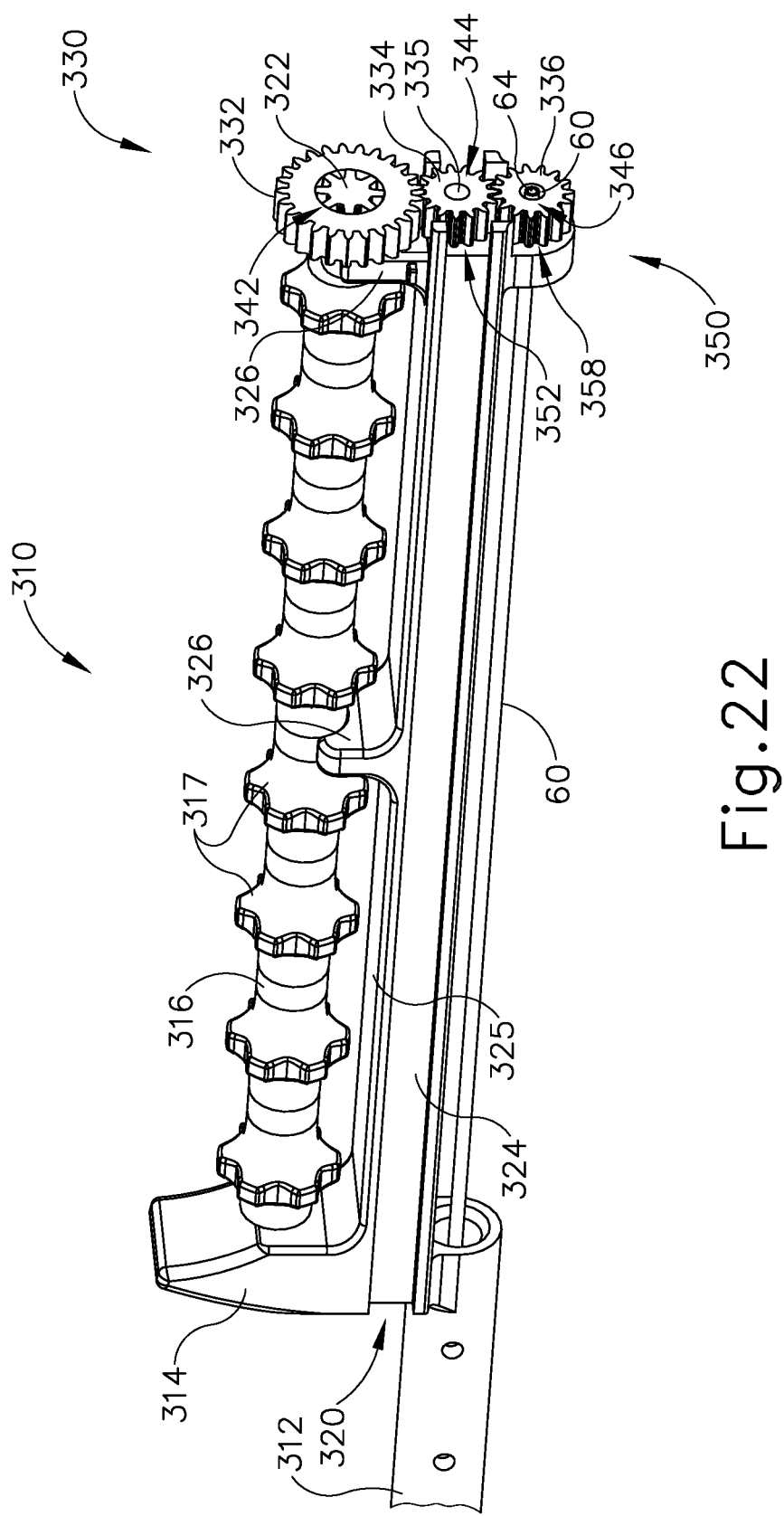
FIG. 22 depicts a cross-sectional perspective view of the guidewire movement assembly of FIG. 20, taken along line 23-23 of FIG. 20.
Figure 23:
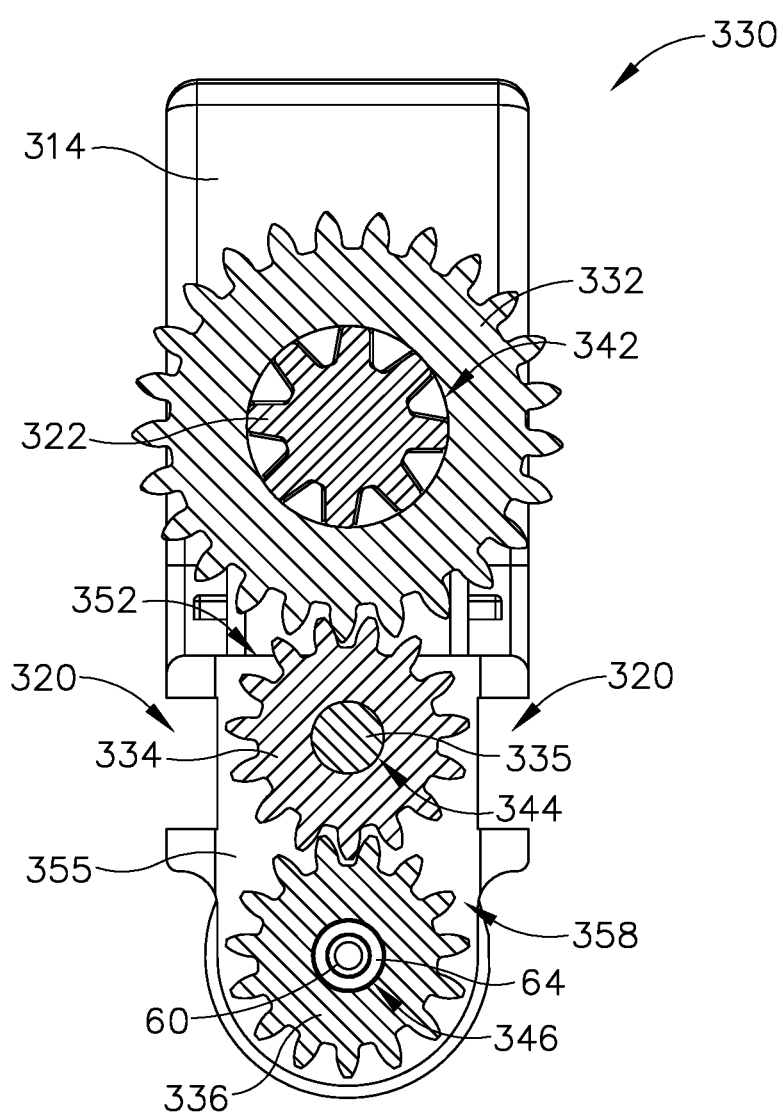
FIG. 23 depicts a cross-sectional front elevational view of the guidewire movement assembly of FIG. 20, taken along line 23-23 of FIG. 20.

Primary gear (332), idler gear (334), and secondary gear (336) each define a bore (342, 344, 346) respectively. As best seen in FIGS. 21-22, bore (342) of primary gear (332) is dimensioned for an interference fit with gear coupling member (322) of rotating member (316). Therefore, rotation of rotating member (316) also rotates primary gear (332) about the longitudinal axis of rotating member (316). While in the current example, primary gear (332) is unitarily coupled with gear coupling member (322) via an interference fit, any other suitable unitary connection of gear coupling member (322) and primary gear (322) may be used as would be apparent to one having ordinary skill in the art in view of the teachings herein.

Idler gear (334) is partially housed within cavity (358) of gear housing (350) such that a portion of idler gear (334) extends above opening (352). Idler gear (334) is pivotally coupled with housing members (355) via pin (335), bore (344), and pin holes (354). Therefore, idler gear (334) is operable to rotate about an axis defined by pin (335) within cavity (358) of gear housing (350). Idler gear (334) and primary gear (332) are dimensioned such that a top portion of idler gear (334) meshes with a bottom portion of primary gear (332) when fully assembled. Therefore, rotation of primary gear (332) in a first angular direction may drive rotation of idler gear (334) in a second, opposite, angular direction.

Secondary gear (334) is housed within cavity (358) of gear housing (350). In the current example, secondary gear (334) is pivotally coupled with housing members (355) via shrink tubing attachment (64), guidewire hole (356), and bore (346). As mentioned above, the inner diameter of shrink tubing attachment (64) may be dimensioned for an interference fit with the outer diameter of guidewire (60) such that shrink tubing attachment (64) and guidewire (60) are unitarily connected. While in the current example, shrink tube attachment (64) is used to couple guidewire (60) with secondary gear (334), any other suitable guidewire attachment may be used as would be apparent to one having ordinary skill in the art in view of the teachings herein. For instance, shrink tube attachment (64) may be replaced with a tubing coupled with guidewire (60) through any form of bonding. Such form of bonding may include adhesives; interference fit via crimping, swaging, ovalized opening, or an intermediate tubing; or a tubing fitting such as a luer fitting, a friction fit with an overmolded elastomeric material, a metal annular spring, or an o-ring, etc.

Additionally, bore (346) is dimensioned for an interference fit with the outer diameter of shrink tube attachment (64) such that shrink tubing attachment (64) and secondary gear (336) are unitarily connected. Shrink tubing attachment (64) is also rotationally housed within guidewire hole (356), such that shrink tubing attachment (64) is vertically supported by guidewire hole (356), but still rotatable relative to housing members (355). Therefore, secondary gear (336) is rotatably coupled with gear housing (350) via shrink tubing attachment (64). It should be understood that the outer diameter of shrink tube attachment (64) is small enough to promote rotation along the longitudinal axis of shrink tube attachment (64) relative to guidewire hole (356) of gear housing (355). In other words, shrink tube attachment (64) is dimensioned small enough to be rotationally housed within housing members (355), yet large enough to be unitarily coupled to secondary gear (336). Therefore, secondary gear (336) is rotatably coupled with gear housing (350) via shrink tubing attachment (64).

As mentioned above, secondary gear (336) is rotatably housed between housing members (355) while housing members (355) are unitarily coupled to elongate body (324). Additionally, shrink tubing attachment (64) and guide wire (60) are unitarily coupled to secondary gear (336). Therefore, if elongate body (324) translates relative to handle assembly (102), housing members (355) may also drive secondary gear (336), shrink tubing attachment (64), and guide wire (60) with elongate body (324). In other words, guide wire (60) may translate relative to handle assemble (102) as determined by elongate body (324).

While in the present example, an interference fit is used to unitarily couple secondary gear (336) with shrink tubing attachment (64), as well as guidewire (60) with shrink tubing attachment (64), any other suitable coupling means may be used as would be apparent to one having ordinary skill in the art in view of the teachings herein. Additionally, while shrink tubing attachment (64) is used in connection with guidewire (60), it should be understood that shrink tubing attachment (64) may be completely omitted such that guidewire (60) contains the necessary properties to unitarily couple with secondary gear (336) and to rotatably couple with housing member (355).

Secondary gear (336) is dimensioned such that a top portion of secondary gear (336) meshes with a bottom portion of idler gear (334) when fully assembled. Therefore, as rotation of primary gear (332) in a first angular direction drives idler gear (334) in a second, opposite, angular direction; idler gear (334) drives secondary gear (336) in the first angular direction. Because shrink tubing attachment (64) and guidewire (60) are both unitarily attached to secondary gear (336), shrink tubing attachment (64) and guidewire (60) both rotate in the first angular direction with secondary gear (336).

In an exemplary use, an operator may rotate rotating member (316) about its own longitudinal axis in a first angular direction through manipulation of rotational grips (317). Because rotating member (316) is unitarily connected to primary gear (332) via gear coupling member (322), primary gear (332) also rotates in the first angular direction. Due to the bottom portion or primary gear (332) meshing with the top portion of idler gear (334), idler gear (334) rotates in a second, opposite angular direction. Due to the bottom portion of idler gear (334) meshing with top portion of secondary gear (336), secondary gear (336) rotates in the first angular direction. Finally, because secondary gear (336) is unitarily coupled with shrink tubing attachment (64) and guidewire (60), shrink tubing attachment (64) and guidewire (60) also rotate in the first angular direction. In other words, rotation of rotating member (316) about its respective longitudinal axis in a first angular direction also rotates guidewire (60) about its respective longitudinal axis in the first angular direction.

It should be understood that any suitable kind of gears may be used for primary gear (332), idler gear (334), and secondary gear (336) as would be apparent to one having ordinary skill in the art in view of the teachings herein. By way of example only, gears (332, 334, 336) may have any of the following meshing teeth configurations: herringbone, helical, straight tooth, male and female featured pin and socket, or cogs, radiating pins, hook and loop style features, etc. By way of further example only, gears (332, 334, 336) may be formed of plastic, metal, glass, ceramic, 3D printed materials, etc. In addition, or in the alternative, gears (332, 334, 336) may comprise internal gears, planetary gears, flexible gears, annular contact gears, bevel gears, and/or internally meshing gears. As yet another merely illustrative variation, gears (332, 334, 336) may be substituted with wheels that transfer rotation to each other via friction. For instance, such wheels may transfer rotation via direct contact with each other, via one or more toothed belts, via one or more flat belts, via one or more "V" belts. As yet another merely illustrative variation, gears (332, 334, 336) may be substituted with wheels that transfer rotation to each other via chain, cable, and/or one or more other motion transfer features.

C. Exemplary Guide Member Attachment Assembly

In some instances, it may be desirable to replace removable guide member (50) with a guide member having a different longitudinal profile or bend angle. For instance, it may be desirable to use different versions of guide member (50) with different longitudinal profiles or bend angles, such as guide member (50) of FIGS. 1A-1D and of FIGS. 2A-2C, in order to facilitate use of a single instrument to access to different anatomical structures in a patient (e.g., maxillary sinus ostium, frontal recess, sphenoid sinus ostium, Eustachian tube, etc.). Additionally, it may be desirable to rotate removable guide member (50) relative to handle assembly (102) about the longitudinal axis defined by removable guide member (50), and then rotationally and longitudinally lock removable guide member (50) relative to handle assembly (102) at the desired location.

FIGS. 9-11C show guide member attachment assembly (170). Guide member attachment assembly (170) includes a rotational lock (172), a static body (180), and a collet (190). Rotational lock (172) is rotatably housed within handle assembly (102). In particular, rotational lock (172) may rotate along a path defined by slot (104) of handle assembly (102). As will be described in greater detail below, rotation of rotational lock (172) will selectively lock removable guide member (50) in a fixed position relative to body assembly (102). Rotational lock (172) includes a cylindrical body (174), a lever (176), and a handle (178). Lever (176) unitarily connects handle (178) with cylindrical body (174). Cylindrical body (174) defines a collet channel (173). Cylindrical body (174) also includes a pair of guide locking protrusions (175) extending inwardly of channel (173). Collet channel (173) is dimensioned to receive and lock a distal portion of collet (190).

Static body (180) defines a collet channel (182) that is dimensioned to receive collet (190). Static body (180) also includes a pair of collet lock protrusions (184) extending inwardly of channel (182). Static body (180) is housed and fixed within handle assembly (102).

Collet includes a pair of leaves (192) that define slots (194). Collet (190) also defines a guide member channel (196) that is dimensioned to selectively receive open proximal end (54) of removable guide (50). Collet (190) is housed and fixed within static body (180). Additionally, collet (190) extends into channel (173) of rotational lock (172). Slots (194) of collet receive collet lock protrusions (184) of static body (180) so that collet (190) is rotationally fixed relative to static body (180).

Leaves (192) are made of a resilient material such that leaves (192) may flex toward each other to a locking position when a force is applied; and such that leaves (192) will return to a relaxed position when a force is no longer applied. Leaves (192) are dimensioned to receive removable guide member (50) while leaves (192) are in a relaxed position. Leaves (192) may then flex inwardly to a locking position in order to grip open proximal end (54) of removable guide member (50).

Figure 11A:
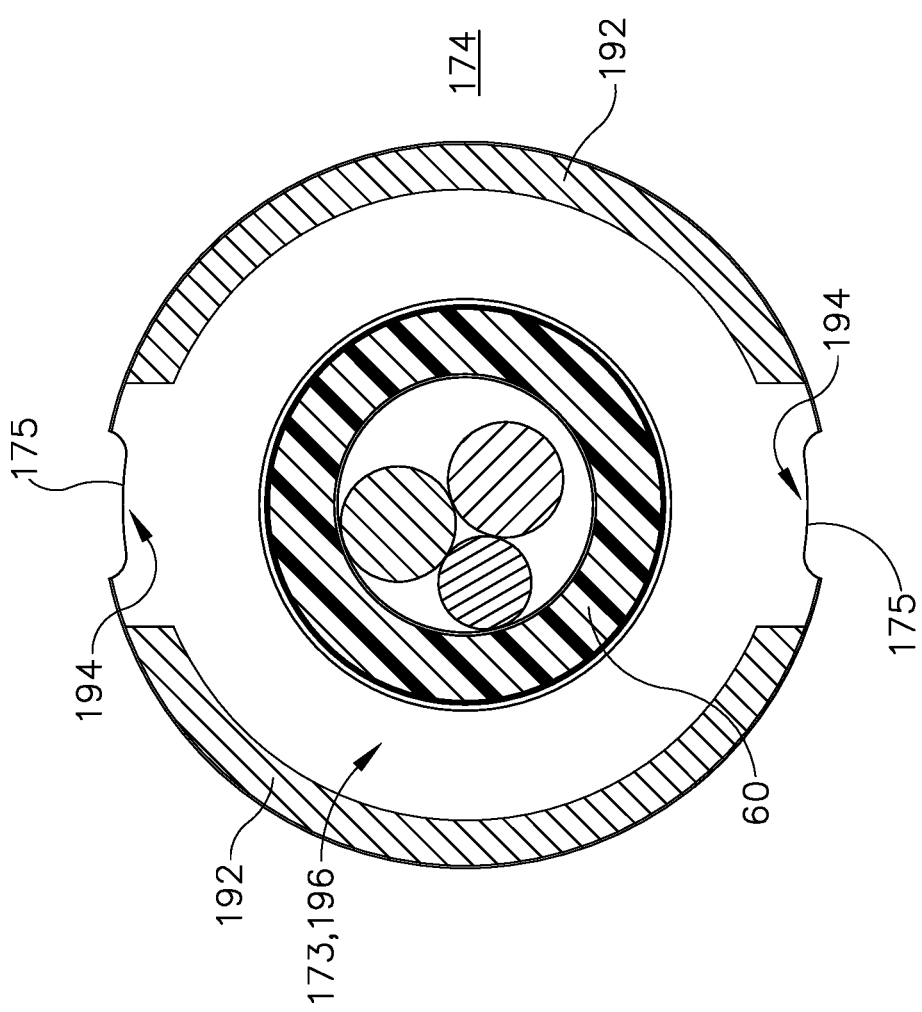
FIG. 11A depicts a cross-sectional front view of the guide member attachment assembly of FIG. 9, where the removable guide member is detached from the guide member attachment assembly.
Figure 11B:
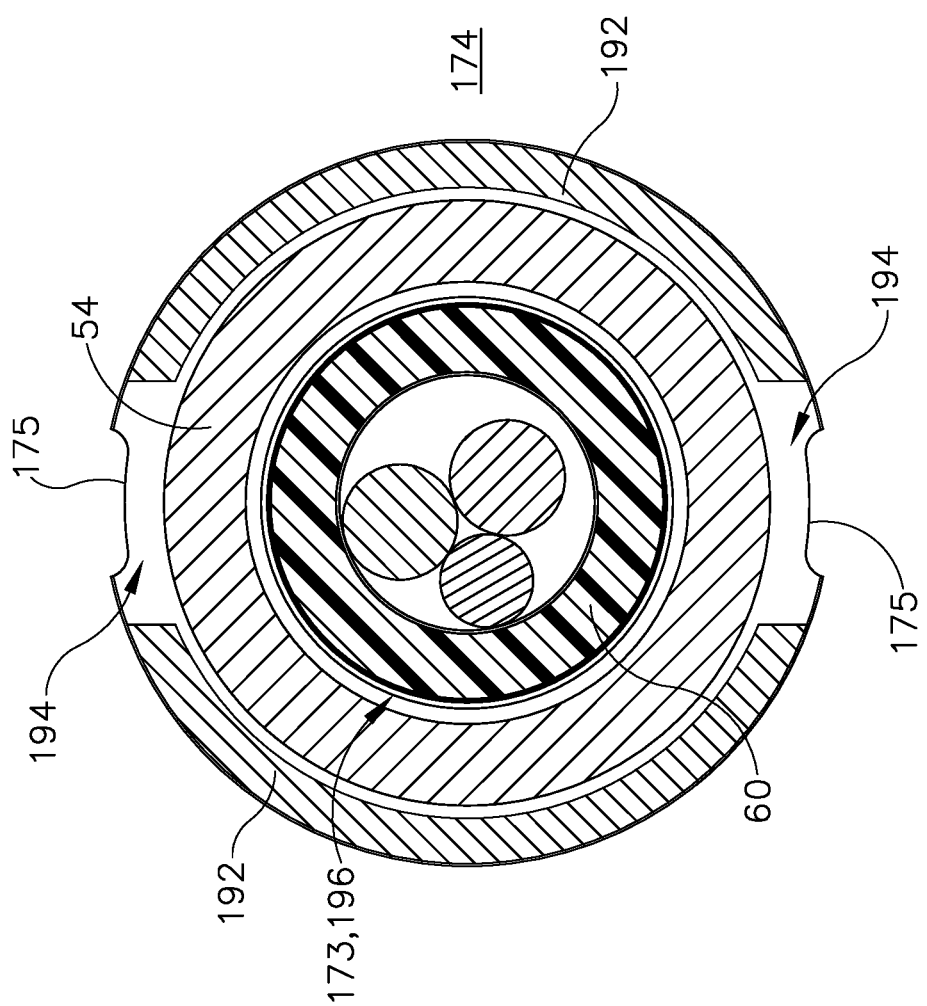
FIG. 11B depicts a cross-sectional front view of the guide member attachment assembly of FIG. 9, where the removable guide member is inserted into the guide member attachment assembly.
Figure 11C:
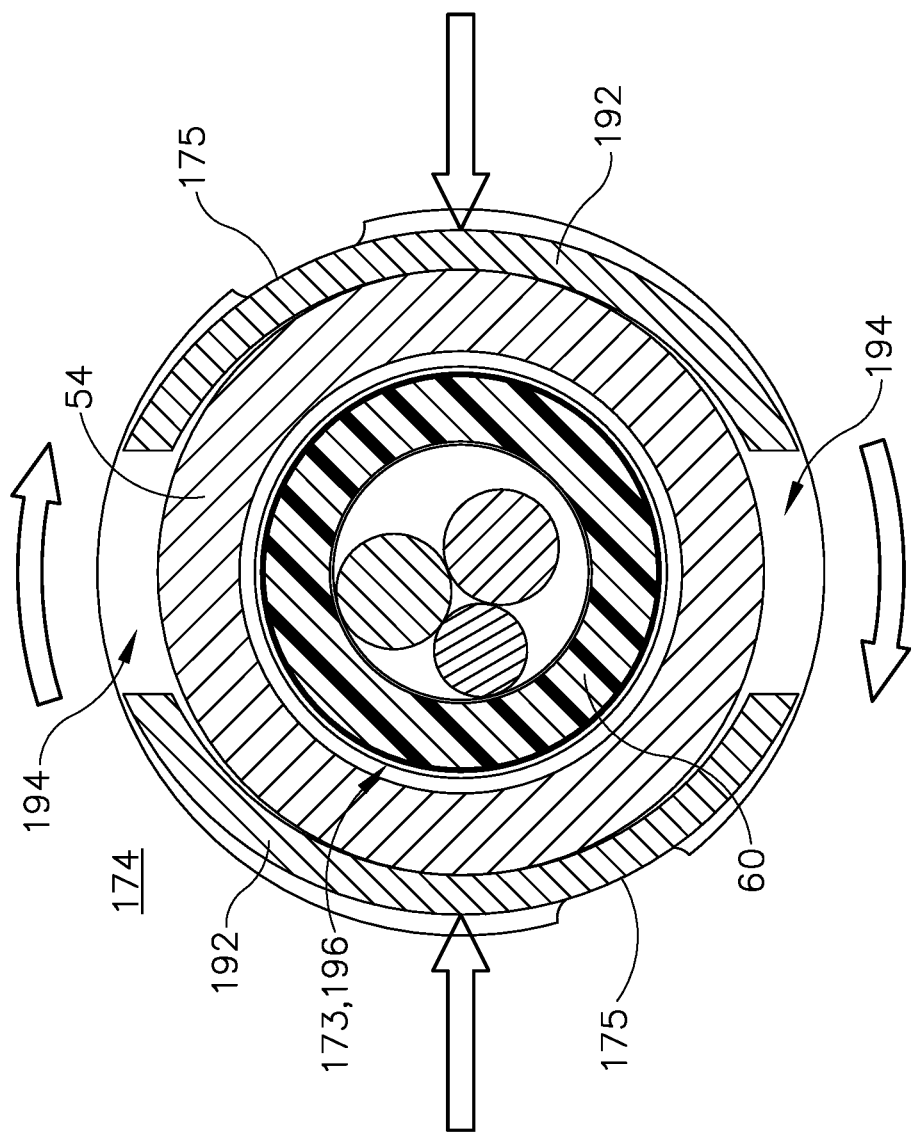
FIG. 11C depicts a cross-sectional front view of the guide member attachment assembly of FIG. 9, where the removable guide member is attached to the guide member attachment assembly.

Guide locking protrusions (175) are dimensioned to rest within slots (194) when rotational lock (172) is in a first angular position, as seen in FIGS. 11A-11B. Additionally, guide locking protrusions (175) are configured to make contact with the outside of leaves (192) when rotational lock (172) is in a second angular position, as seen in FIG. 11C. Contact between leaves (192) and guide locking protrusions (175) will force leaves (192) to a locking position. In other words, the angular position of rotational lock (172) may determine whether leaves (192) of collet (190) are in a locking position or a relaxed position.

Figure 10A:
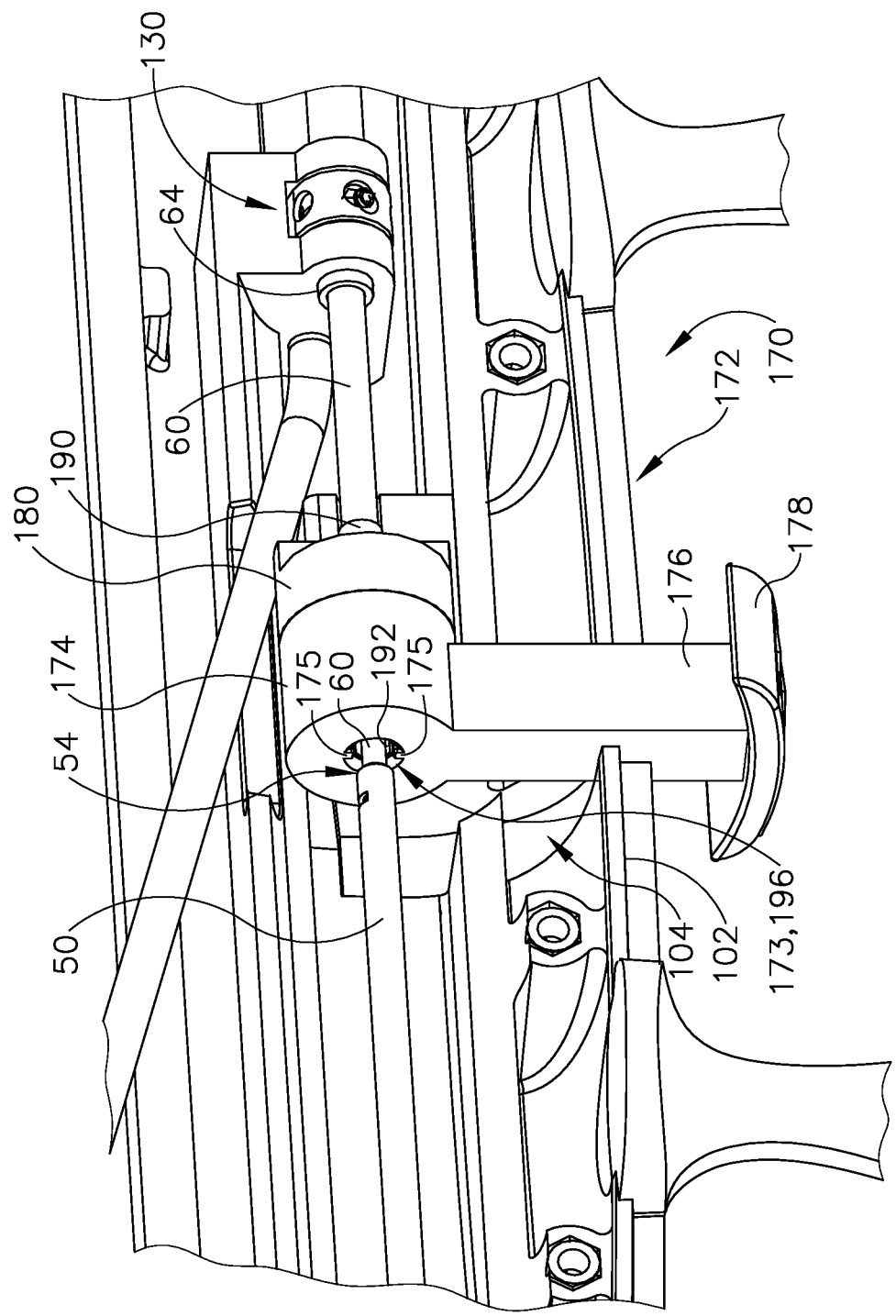
FIG. 10A depicts a perspective view of the dilation instrument of FIG. 1A, where the removable guide member is detached from the guide member attachment assembly, with the dilation catheter movement assembly removed for clarity.

FIGS. 10A-11C show removable guide member (50) being inserted and locked into guide member attachment assembly (170). FIGS. 10A-10C do not show dilation catheter movement assembly (140) for purposes of clarity. Therefore, it should be understood that removable guide member (50) is inserted into catheter shaft (144) when being installed into guide member attachment assembly (170).

First, as shown in FIGS. 10A and 11A, a user may insert removable guide member (50) within catheter shaft (144) and slide removable guide member (50) toward the distal end of rotational lock (172). Proximal open end (54) of removable guide member (50) will exit the proximal open end of catheter shaft (144). At this point, proximal open end (54) of removable guide member (50) is not within collet (190) or rotational lock (172).

Figure 10B:
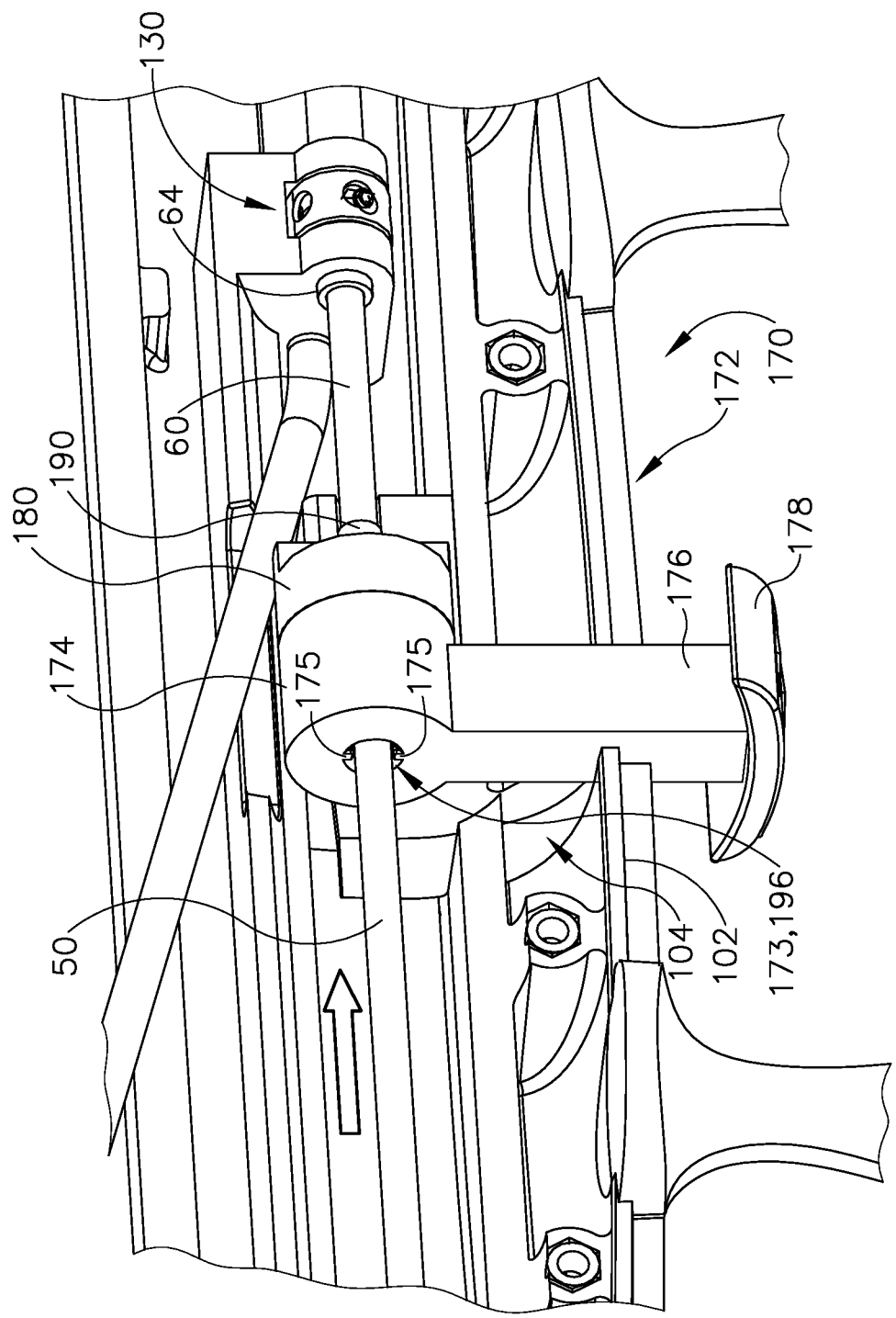
FIG. 10B depicts a perspective view of the dilation instrument of FIG. 1A, where the removable guide member is inserted into the guide member attachment assembly, with the dilation catheter movement assembly removed for clarity.

Second, as shown in FIGS. 10B and 11B, a user may insert proximal open end (54) of removable guide member (50) within a portion of guide member channel (196) defined by leaves (192) of collet (190). As emphasized in FIGS. 11A-11B, it should be understood that rotational lock (172) is at a first angular position where guide locking protrusions (175) rest within slots (194) defined by leaves (192) of collet (190). At this moment, a user may adjust the longitudinal and rotational locations of guide member (50) relative to handle assembly (102). For instance, a user may rotate guide member (50) about the longitudinal axis of guide member (50) in order to place open distal end (52) of removable guide member (50) to a desired location. This may be especially beneficial if guide member (50) has a curved longitudinal profile, such as that shown in FIG. 2A.

Figure 10C:
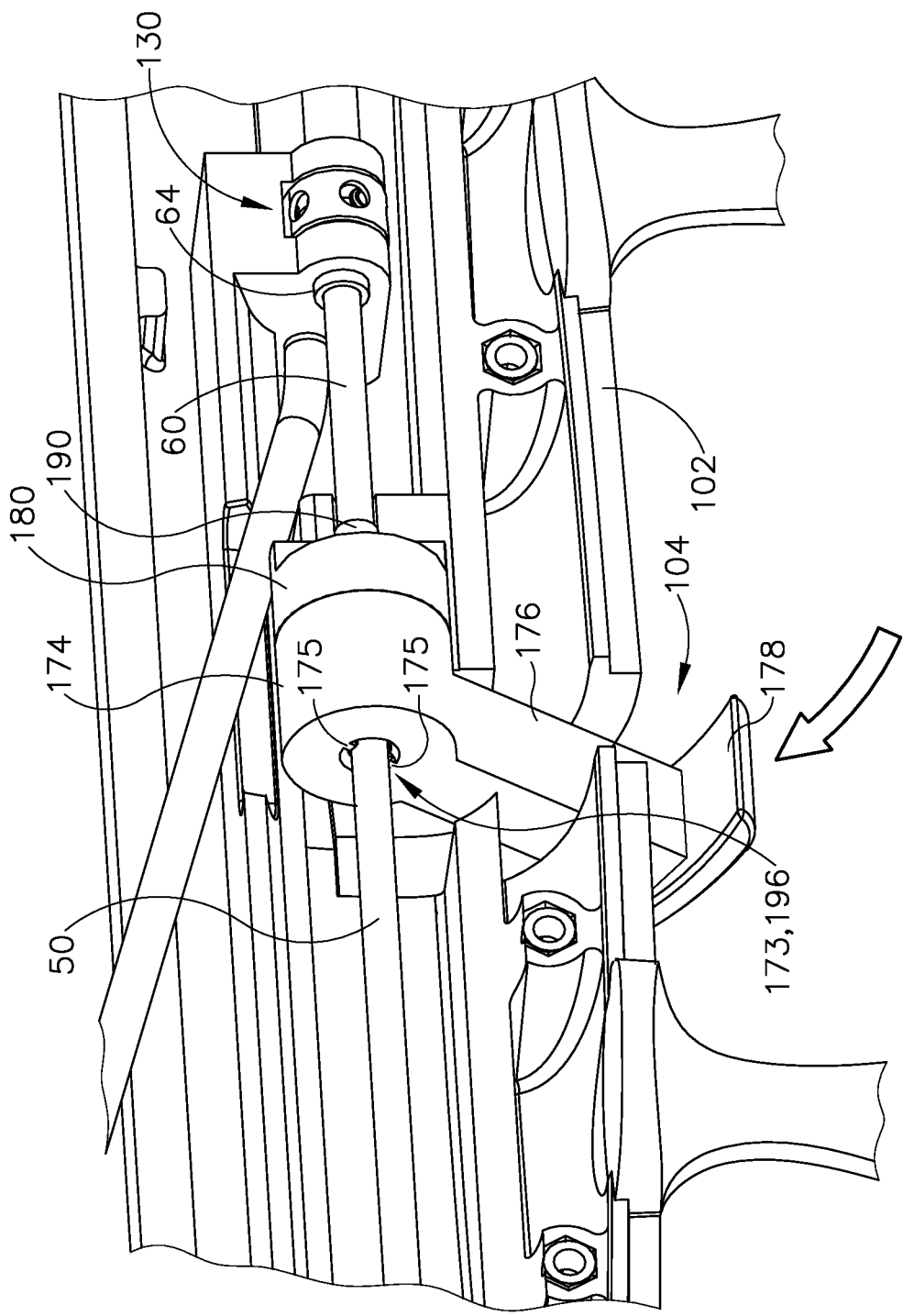
FIG. 10C depicts a perspective view of the dilation instrument of FIG. 1A, where the removable guide member is attached to the guide member attachment assembly, with the dilation catheter movement assembly removed for clarity.

With removable guide member (50) placed in the desired location, a user may rotate rotational lock (172) within slot (104) of handle assembly (102) to a second rotational position, as shown in FIGS. 10C and 11C. As described above, rotation of rotational lock (172) to the second angular position forces guide locking protrusions (175) to make contact with the outside surface of leaves (192). The contact between guide locking protrusions (175) and the outside surface of leaves (192) forces leaves (192) to flex inwardly to a locking position, thereby gripping open proximal end (54) of removable guide member (50). Contact between leaves (192) of collet (190) and removable guide member (50) provide a frictional braking force on removable guide member (50). The frictional braking force between leaves (192) and removable guide member (50) effectively lock the position of removable guide member (50) relative to handle assembly (102). A user may then use instrument (100) in the desired operation, with the ability to slide catheter shaft (144) over removable guide member (50) in order to access the desired location of a patient.

When a user no longer needs a particular removable guide member (50), or desires to replace the current removable guide member (50) with a different guide member (50), a user may simply rotate rotational lock (172) to the first angular position, as shown in FIGS. 10B and 11B, thereby returning leaves (192) to the relaxed position and unlocking removable guide member (50) from collet (190). A user may then remove removable guide member (50) from guide member attachment assembly (170), catheter shaft (144), and the rest of instrument (100).

While two leaves (192) and two guide locking protrusions (175) are utilized in the current example, it should be understood that any number of leaves (192) and guide locking protrusions (175) may be utilized as would be apparent to one having ordinary skill in the art in view of the teachings herein. While in the current example, rotational lock (172) rotates guide locking protrusions (175) in order to make contact with leaves (192), it should be understood that guide locking protrusions (175) may axially translate in order to make contact with leaves (192).

It should also be understood that while the current example utilizes a rotational lock (172) to rotate guide locking protrusions (175) to cam against leaves (192) of collet (190) in order to lock removable guide member (50), any other suitable mechanisms may be used in order to selectively lock removable guide member (50) relative to handle assembly (102) as would be apparent to one having ordinary skill in the art in view of the teachings herein. For instance, instead of rotating rotational lock (172), rotational lock may be biased to a first locking position. A frictional braking force may be applied between biased rotational lock (172) and static body (180) due to misalignment of channels (173, 182), in order to lock removable guide member (50) inserted between channels (173, 182). Alternatively, a frictional braking force may be applied to collet (190) instead of directly to removable guide member (50). Lock (172) may then be actuated, either linearly or rotationally, such that channels (173, 182) align in order to unlock and remove removable guide member (50).

As another merely illustrative example, rotational lock (172) may be reconfigured such that lever (176) and handle (178) are replaced with a knob that is positioned remotely from cylindrical body (174) (e.g., distal to body (174) or proximal to body (174)). Such a knob may be coupled with cylindrical body (174) via longitudinally extending members, a sheath, and/or some other component that provides rotation of cylindrical body (174) in response to rotation of the knob. As another merely illustrative example, rotational lock (172) may be reconfigured to include a collet that is rotated relative to static collet lock protrusions. As another merely illustrative example, rotational lock (172) may be reconfigured to include a locking bolt or pin. In some such versions, removable guide member (50) includes a recess or slot that receives a pin, which is inserted radially into the recess or slot of the removable guide member (50). In some such versions, the pin is resiliently biased to enter the recess or slot of the removable guide member (50). In addition, or in the alternative, the pin may have threading that controls insertion of the pin into the recess or slot of the removable guide member (50). In addition, or in the alternative, the pin may have a round or flat fork-shaped feature that engages removable guide member (50) on both sides of the longitudinal axis. As another merely illustrative example, the pin may be aligned with the longitudinal axis of removable guide member (50). Alternatively, the pin may be tangent to the longitudinal axis of removable guide member (50). Additionally, or alternatively, removable guide member (50) may have threading while guide member attachment assembly (170) may have complementary threading in order to couple removable guide member (50) and guide member attachment assembly (170). Still other suitable variations will be apparent to those of ordinary skill in the art in view of the teachings herein.

Open end (54) of removable guide member (50) may be fastened with ball-bearing style detents that are cam tightened into knurling or detents of the outer diameter of open end (54) when making contact within either or both channels (173, 182), or collet (192). By way of example only, detents may be in the form of a series of depressions in a molded proximal end. By way of further example only, detents may be in the form of a radial groove into which latching features extend to create a mechanical inference.

As another merely illustrative example, removable guide member (50) may be attached to guide member attachment assembly (170) through use of a compressible elastomeric ring that is axially compressed to cause interference between guide member attachment assembly (170) and removable guide member (50). As yet another merely illustrative example, removable guide member (50) may be attached with bayonet style features that are rotated and retained in a rotating guide member attachment assembly (170) with interference features.

Magnets fixed to handle assembly (102) may be selectively engaged with complementary magnets fixed to removable guide member (50) in order to fix removable guide member (50) to handle assembly (102). Magnets may also be used as actuating devices, instead of being fixed to handle assembly (102), to attract or repel magnetized removable guide (50). Magnets may be used to prevent rotation of removable guide member (50) by inserting magnets with opposite poles. Magnets of like poles may be positioned to push removable guide member (50) into guide member attachment assembly (170).

Collet (190) may be made out of any suitable material, including metal, polymer, elastomer, any combination thereof, and/or any other suitable material(s) as would be apparent to one having ordinary skill in the art in view of the teachings herein.

Open proximal end (54) of removable guide member (50) might have a decreasing inner diameter formed from a fluid inflated bladder. Such a bladder may be annular or non-coaxial.

As yet another merely illustrative example, removable guide member (50) may be attached using actuated bimetal features or collet (190) that are actuated when warmed to either connect or disconnect removable guide member (170). Still other suitable variations of the above-described components will be apparent to those of ordinary skill in the art in view of the teachings herein.

II. Exemplary Alternative Dilation Instrument

Figure 12:
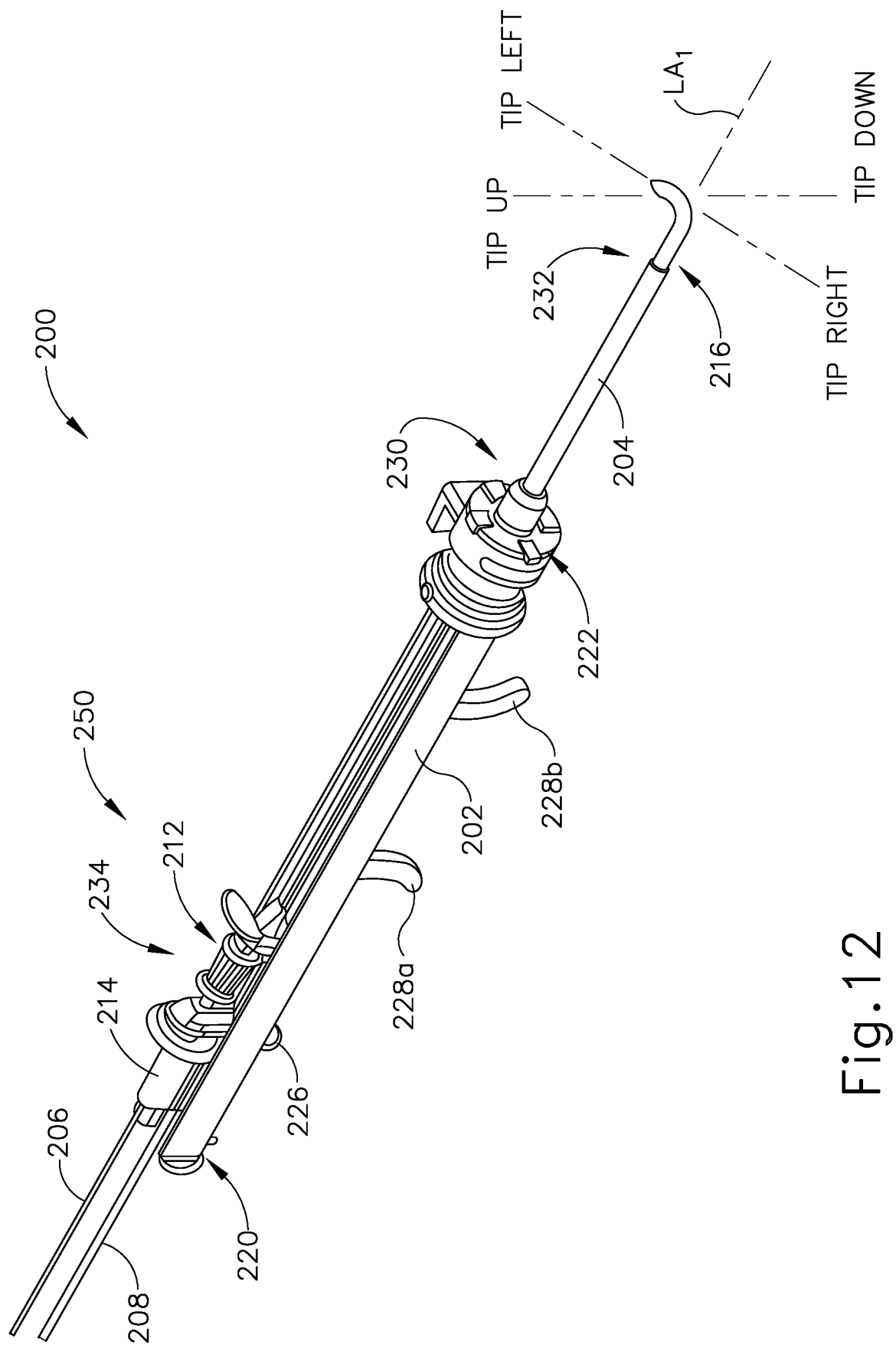
FIG. 12 depicts a perspective view of an another exemplary dilation instrument.
Figure 13:
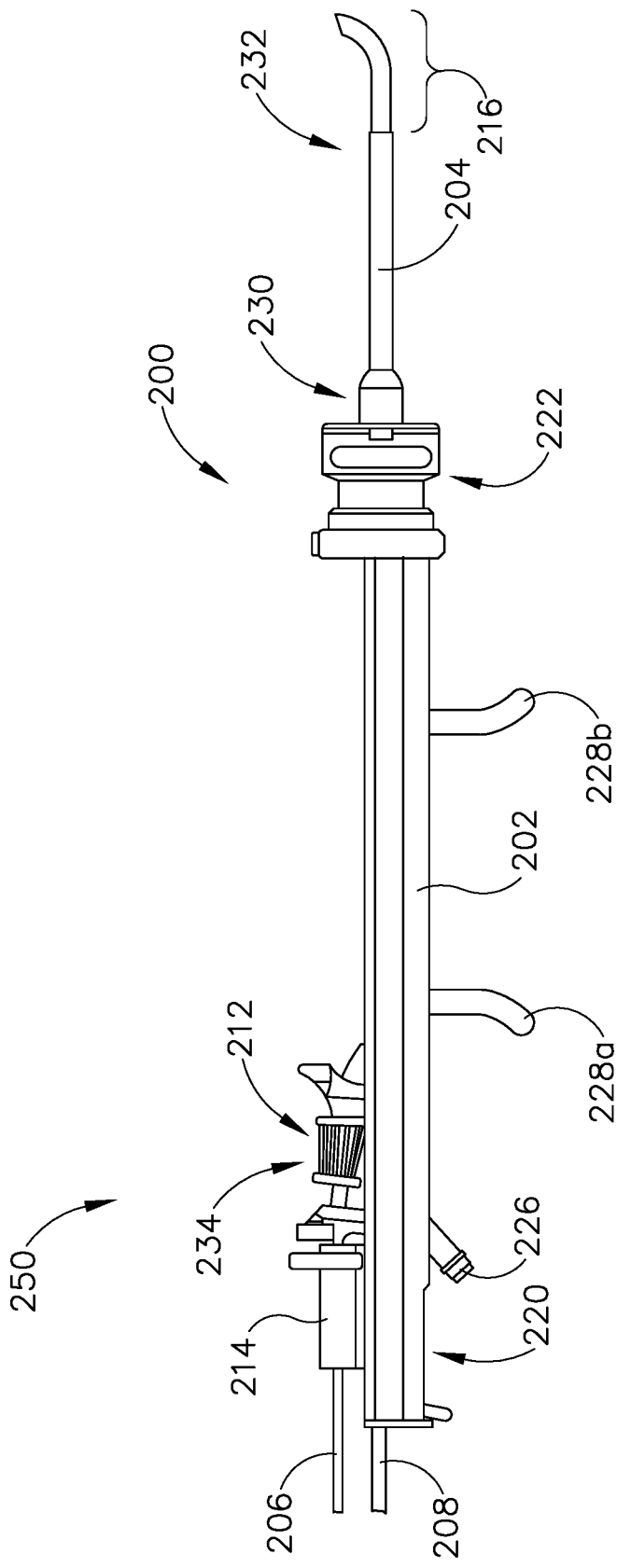
FIG. 13 depicts a side elevational view of the dilation instrument of FIG. 12.
Figure 14:
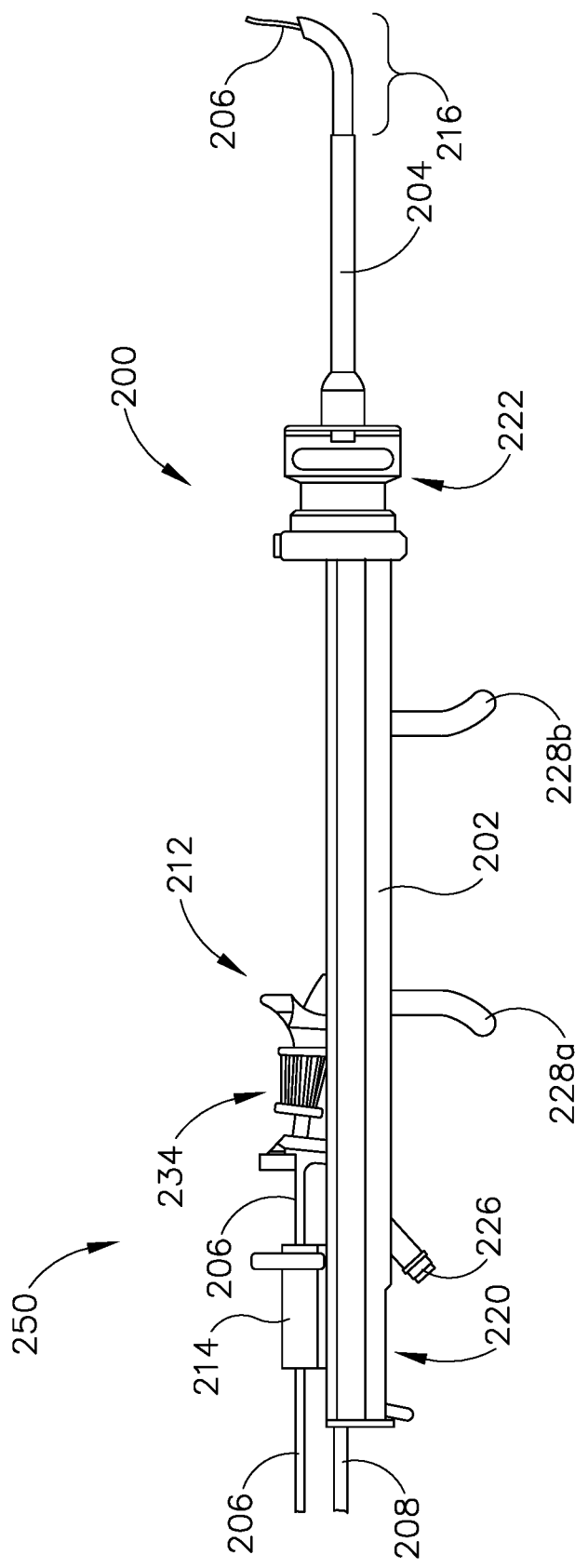
FIG. 14 depicts a side elevational view of the dilation instrument of FIG. 12 with a guidewire of the instrument advanced distally.

FIGS. 12-14 show another exemplary instrument (200) that may be used to treat a paranasal sinus drainage passageway (e.g., a frontal recess, a maxillary sinus ostium, a sphenoid sinus ostium, etc.) and/or some other anatomical passageway (e.g., Eustachian tube, etc.). Instrument (200) of this example includes a handle (202), a guide catheter (204), a detachable guide tip (216) (shown with a curved (angled) tip in a "tip up" orientation), and an actuating assembly (250). Actuating assembly (250) includes a guidewire (206), a dilation catheter (208), a guidewire movement assembly (212), a dilation catheter movement actuator (214), and a guidewire support (118) (see FIGS. 15-16). FIG. 12 includes a series of markers depicting alternative orientations of guide tip (216). In particular, a "tip up," a "tip left," a "tip down," and a "tip right" orientation of guide tip (216) are shown in FIG. 12.

As shown in FIGS. 12-14, handle (202) of the present example includes a proximal end (220) and a distal end (222); and defines a longitudinal axis (LA1) along the length of handle (202). Handle (202) further includes a fluid port (226) and finger anchoring pegs (228a, 228b). In the present example, fluid port (226) is configured to couple with a source of suction to provide suction via guide catheter (204). In addition or in the alternative, fluid port (226) may be coupled with a fluid source to provide irrigation. Other suitable ways in which fluid port (226) may be made and used will be apparent to those of ordinary skill in the art in view of the teachings herein.

Handle (202) is sized and shaped such that instrument (200) can be manipulated and operated by a user (such as a physician) in a convenient and efficient single-handed manner if so desired, with finger anchoring pegs (228a, 228b) promoting gripping of handle (202) with a single hand. Handle (202) can be formed of any suitable material including, for example, polycarbonate and ABS (acetonitrile butadiene styrene) and can be manufactured using any suitable technique including, for example, injection molding of two clamshell handle halves. Various suitable materials and methods that may be used to manufacture handle (202) will be apparent to those of ordinary skill in the art in view of the teachings herein.

Guide catheter (204) of this example is attached to distal end (222) of handle (202) and defines an inner lumen (i.e., inner passage) that is configured to slidably receive dilation catheter (208). Guide catheter (204) extends along longitudinal axis (LA1) and has a proximal end (230) and a distal end (232). Guide catheter (204) can be formed of any suitable materials including, for example, stainless steel, polymeric materials, and combinations thereof.

Detachable guide tip (216) is configured for removable attachment to, and detachment from, distal end (232) of guide catheter (204). However, detachable tips can be attached and detached from instrument (200) at any suitable location. For example, guide tip (216) can be attached anywhere along guide catheter (204) or at the distal end of handle (202). Guide tip (216) can be formed of any suitable material including, for example, stainless steel, polymeric materials and combinations thereof. It should also be understood that guide catheter (204) may have an integral tip that is pre-bent, malleable, or otherwise formed such that a separate, detachable guide tip (216) may be omitted from instrument (200). In other words, detachable guide tip (216) is merely optional.

Figure 15:
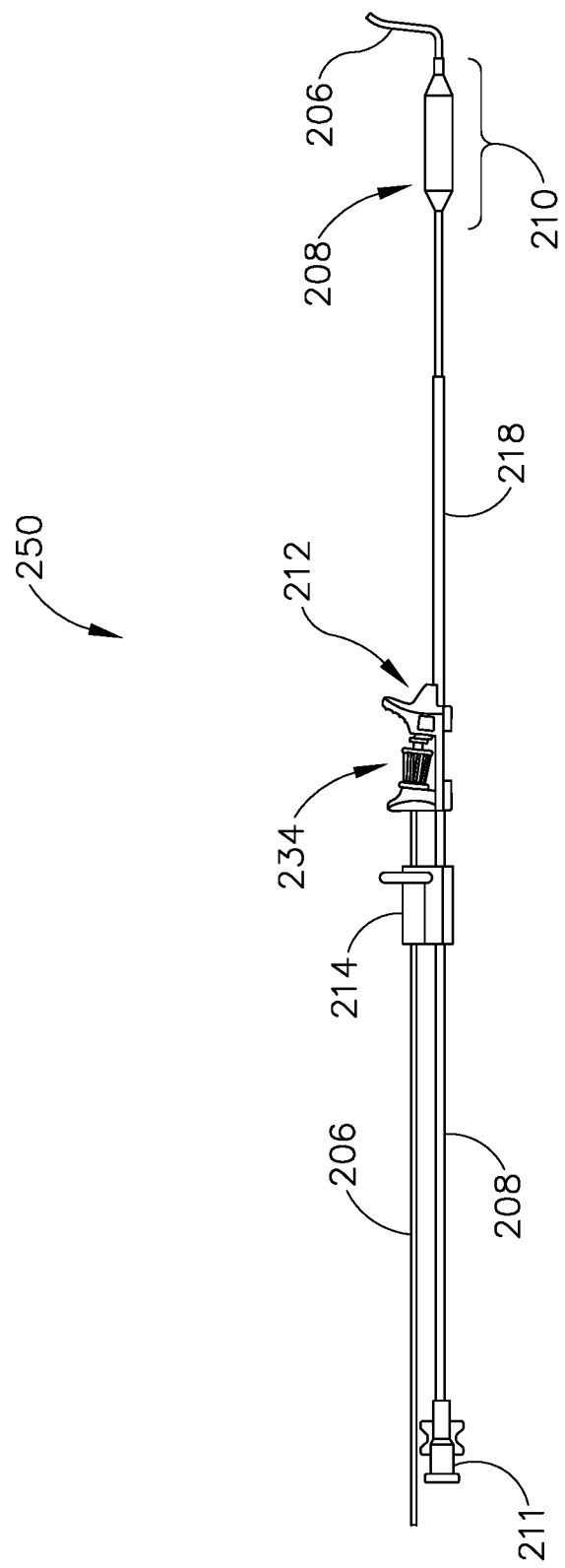
FIG. 15 depicts a side elevational view of the actuating assembly of the dilation instrument of FIG. 12, with a working balloon segment of the dilation catheter shown in an inflated state.
Figure 16:
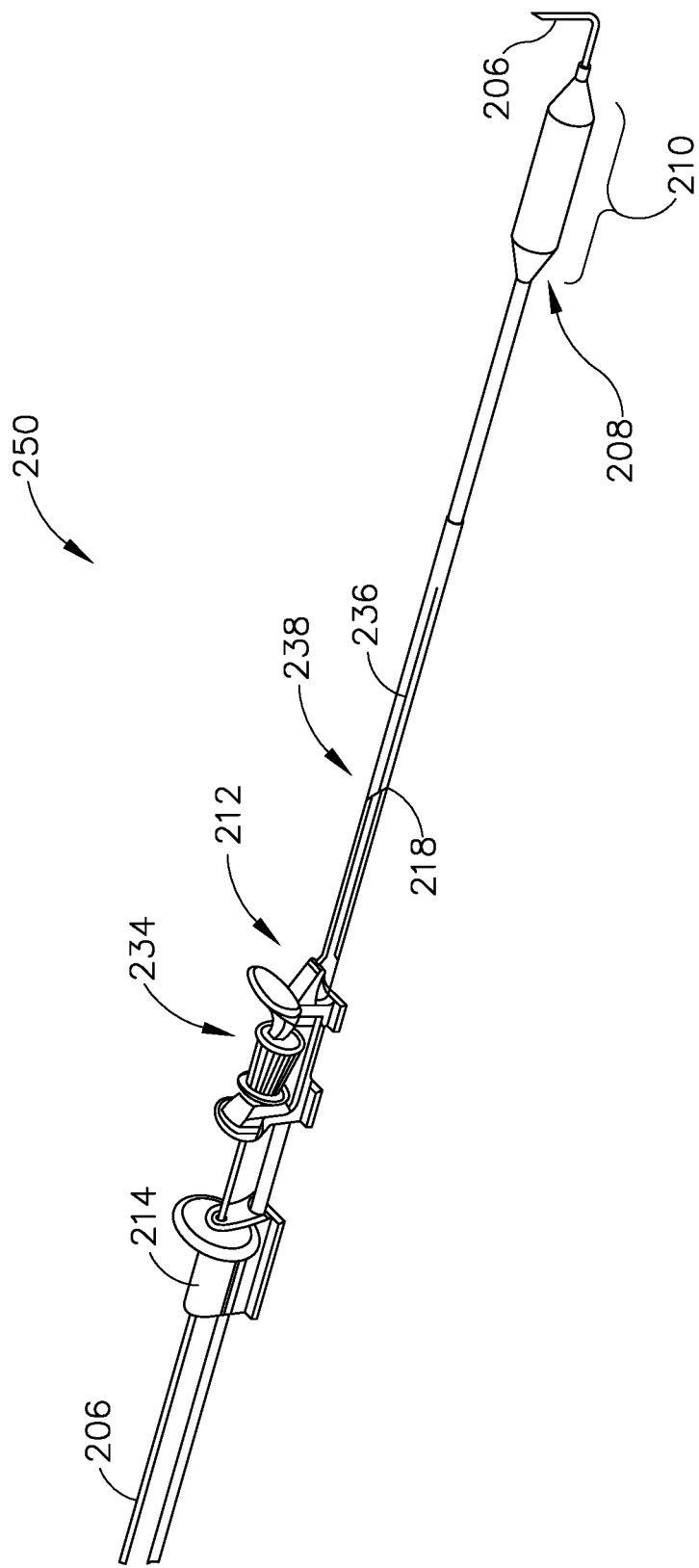
FIG. 16 depicts a perspective view of the actuating assembly of FIG. 15, with the working balloon segment of the dilation catheter shown in an inflated state.

As best seen in FIGS. 15-16, dilation catheter (208) of the present example comprises an inflatable balloon (210) and an inflation port (211). Dilation catheter (208) further defines a first inner lumen and a second inner lumen. The first inner lumen of dilation catheter (208) distally terminates in balloon (210) and provides a path for fluid communication between inflation port (211) and balloon (210). Inflation port (211) may thus be coupled with a fluid source to provide selective inflation of balloon (210) in accordance with the teachings herein. The second inner lumen of dilation catheter (208) extends all the way to the open distal end of dilation catheter (208) and provides a passageway to slidably receive guidewire (206) as described below. Dilation catheter (208) is slidably disposed at least partially in handle (202) and in the lumen of guide catheter (204). Dilation catheter (208) may be configured and operable in accordance with any suitable dilation catheters known to one skilled in the art.

During operation of instrument (200), dilation catheter (208) may be translated between a proximal position and a distal position. In particular, dilation catheter (208) may be longitudinally advanced and retracted relative to handle (202) and through the lumen of guide catheter (204). When dilation catheter (208) is in the proximal position, balloon (210) may be positioned within the lumen of guide catheter (204), proximal to the distal end (232) of guide catheter (204). When dilation catheter (208) is in the distal position, balloon (210) may be positioned distal to the distal end (232) of guide catheter (204). In versions where guide tip (216) is included, balloon (210) may also be positioned distal to the distal end of guide tip (216) when dilation catheter (208) is in the distal position.

Dilation catheter movement actuator (214) is operatively disposed on handle (202) and is operable to provide the above-described longitudinal advancement and retraction of dilation catheter (208) between the proximal and distal positions. In particular, dilation catheter movement actuator (214) provides such movement by longitudinally sliding along handle (202). Although dilation catheter movement actuator (214) of the present example is described as sliding along the length of handle (202), movement of dilation catheter (208) can be accomplished by any other suitable operation. In some variations, dilation catheter movement actuator (214) is rotatable relative to handle (202) to provide longitudinal advancement and retraction of dilation catheter (208). Various suitable ways in which dilation catheter (208) may be longitudinally advanced and retracted relative to handle (202) and through the lumen of guide catheter (204) will be apparent to those of ordinary skill in the art in view of the teachings herein.

Guidewire (206) of this example is slidably disposed in dilation catheter movement actuator (214), at least partially in handle (202), in guidewire support (218), and in the second inner lumen of dilation catheter (208). Guidewire (206) may be configured and operable in accordance with any suitable guidewire known to one skilled in the art including, for example, an illuminating guidewire that is configured to provide a user with confirmation of sinus access via transillumination. Guidewire support (218) of instrument (200) is operatively disposed within handle (202) and provides additional column strength to guidewire (206), such that guidewire support (218) prevents guidewire (206) from buckling within handle (202) during advancement of guidewire (206) relative to handle (202). As shown in FIG. 16, guidewire support (218) includes a slit-shaped opening (236) into which guidewire (206) is fed by guidewire movement assembly (212). In some versions, guidewire support (218) comprises a hypotube. In addition, or in the alternative, guidewire support (218) may be provided by dilation catheter (208).

Guidewire movement assembly (212) is operatively disposed on handle (202) and is operable to longitudinally advance and retract guidewire (206) relative to handle (202), through guidewire support (218), and through the lumen of guide catheter (204) by longitudinal sliding of guidewire movement assembly (212) along the length of handle (202). FIG. 13 shows guidewire movement assembly (212) and guidewire (206) in a proximal position, where the distal end of guidewire (206) is positioned proximal to the distal end of detachable guide tip (216). In some versions, the distal end of guidewire (206) is also positioned proximal to distal end (232) of guide catheter (204) when guidewire (206) is in a proximal position as shown in FIG. 13.

FIG. 14 shows guidewire movement assembly (212) and guidewire (206) in a distal position, where the distal end of guidewire (206) is positioned distal to the distal end of detachable guide tip (216). It should be understood that guidewire movement assembly (212) may be used to advance the distal end of guidewire (206) through an opening of a paranasal sinus (or some other passageway); and then dilation catheter movement actuator (214) may be used to advance dilation catheter (208) along guidewire (206) to position balloon (210) in the opening of the paranasal sinus as described above. Balloon (210) may then be inflated to dilate the opening of the paranasal sinus.

In the present example, guidewire movement assembly (212) further includes an integrated guidewire locking and rotation knob (234) that is operable to rotate guidewire (206) about the longitudinal axis of guidewire (206). Knob (234) is secured to guidewire (206) such that knob (234) and guidewire (206) rotate unitarily with each other about the longitudinal axis of guidewire (206). Knob (234) is also configured for securely locking and unlocking guidewire (206) to guidewire movement assembly (212). Although guidewire movement assembly (212) of the present example is described as sliding along the length of handle (202), movement of guidewire (206) can be accomplished by any other suitable operation. In some variations, guidewire movement assembly (212) is rotatable relative to handle (202) to provide longitudinal advancement and retraction of guidewire (206). Various suitable ways in which guidewire (206) may be longitudinally advanced and retracted relative to handle (202) and through the second lumen of dilation catheter (208) will be apparent to those of ordinary skill in the art in view of the teachings herein.

In addition to or as an alternative to being constructed and operable in accordance with the above teachings, instrument (200) may be constructed and operable in accordance with at least some of the teachings of U.S. Pub. No. 2012/0071856, entitled "Medical Device and Method for Treatment of a Sinus Opening," published Mar. 22, 2012, issued as U.S. Pat. No. 9,554,817 on Jan. 31, 2017, the disclosure of which is incorporated by reference herein. By way of example only, instrument (200) may include a "clicker" and/or other feature that provides audible and/or tactile feedback as knob (234) is rotated to rotate guidewire (206), as described in U.S. Pub. No. 2012/0071856, issued as U.S. Pat. No. 9,554,817 on Jan. 31, 2017. Of course, various other teachings of U.S. Pub. No. 2012/0071856, issued as U.S. Pat. No. 9,554,817 on Jan. 31, 2017, may also be readily incorporated into instrument (200). In addition, or in the alternative, instrument (200) may be modified in accordance with the various teachings below.

Figure 17:
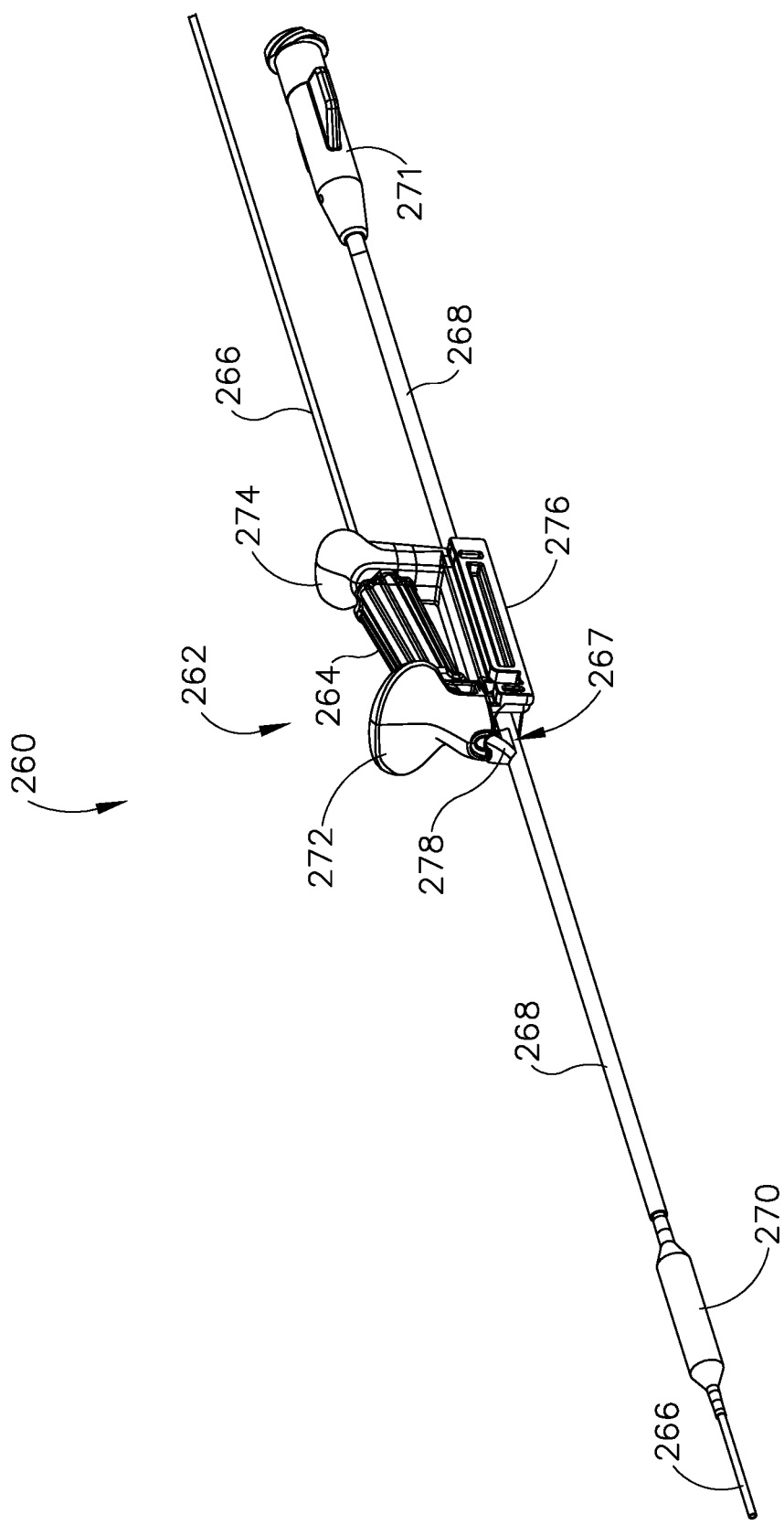
FIG. 17 depicts a perspective view of an alternative actuating assembly that may be readily incorporated into the dilation instrument of FIG. 12.
Figure 18:
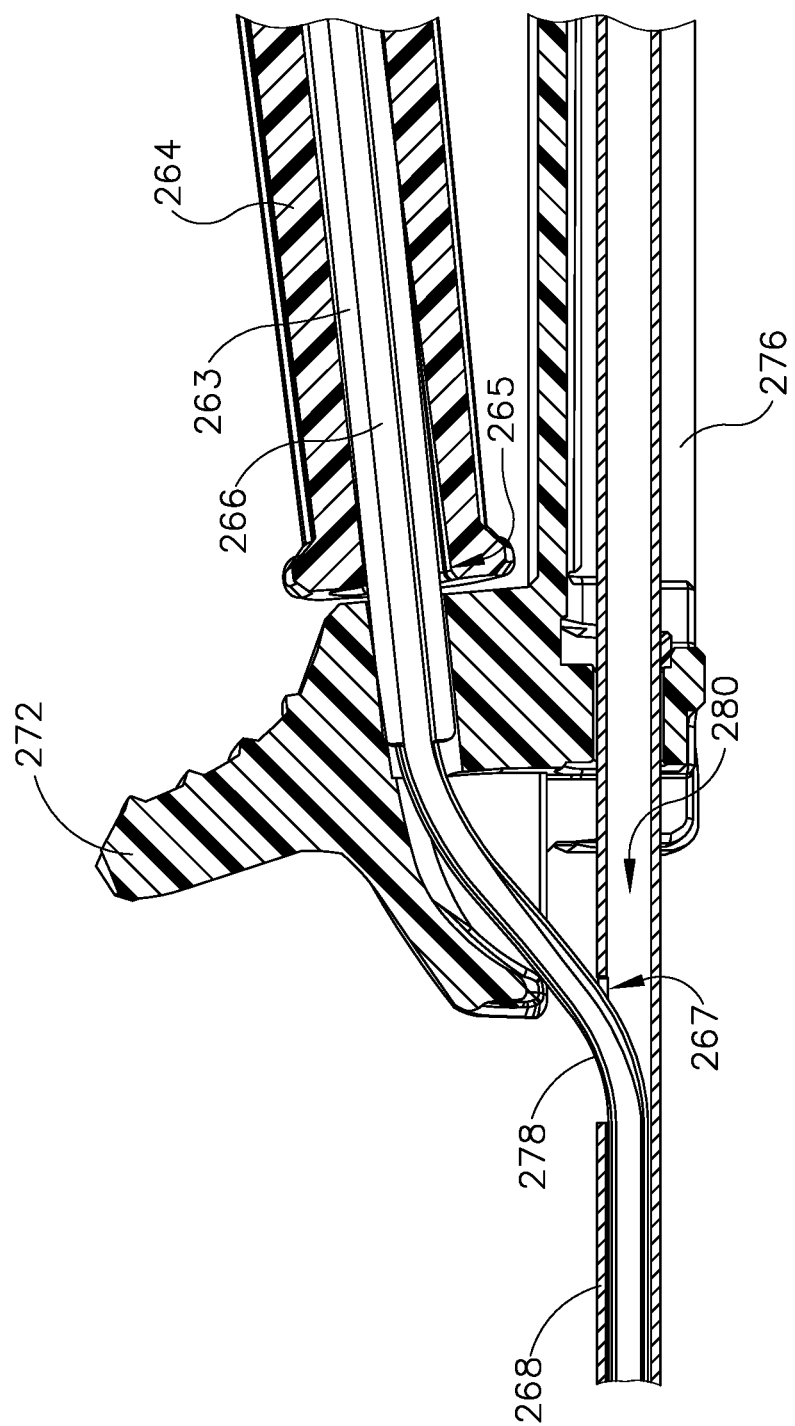
FIG. 18 depicts a side cross-sectional view of the actuating assembly of FIG. 17.
Figure 19:
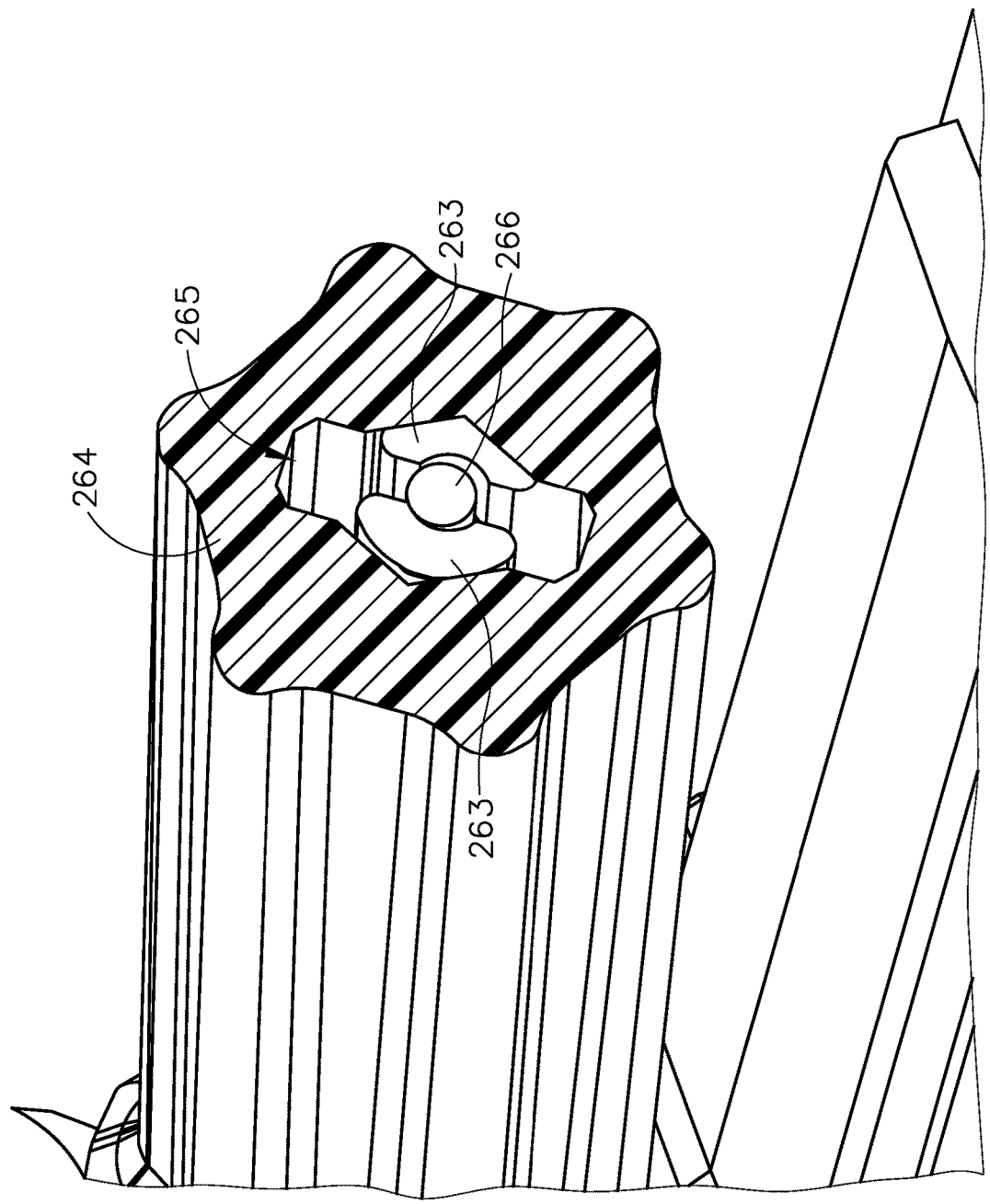
FIG. 19 depicts a perspective cross-sectional view of the integrated guidewire locking and rotation knob of the actuating assembly of FIG. 17.

FIGS. 17-19 show an exemplary alternative actuating assembly (260) that may be readily incorporated into dilation instrument (200) in place of actuating assembly (250). Alternative actuating assembly (260) includes a unitary movement assembly (262), a dilation catheter (268) and a guidewire (266). Guidewire (266) may be substantially similar to guidewire (60, 206) mentioned above. As will be described in greater detail below, unitary movement assembly (262) may incorporate features of both guidewire movement assembly (212) and dilation catheter movement actuator (214).

Unitary movement assembly (262) includes a pommel (272), a cantle (274), an integrated guidewire locking and rotation knob (264) rotationally disposed between pommel (272) and cantle (274), and a body (276). Unitary movement assembly (262) may be slidably coupled to handle (202) via body (276). Body (276) is fixed relative to pommel (272) and cantle (274). Additionally, body (276) is fixed relative to dilation catheter (268). Pommel (272) and cantle (274) allow a user to slide unitary movement assembly (262) relative to handle (202) with a finger. Therefore, a user may unitarily slide dilation catheter (268) and unitary movement assembly (262).

Integrated guidewire locking and rotation knob (264) is substantially similar to integrated guidewire locking and rotation knob (234) described above, with differences described below. Knob (264) it operable to rotate guidewire (266) about the longitudinal axis of guidewire (266) relative to dilation catheter (268). Knob (264) is also configured for securely locking and unlocking guidewire (266) to unitary movement assembly (262), such that guidewire (266) may also translate with dilation catheter (268) and unitary movement assembly (262). As best seen in FIG. 19, integrated guidewire locking and rotation knob (264) further defines a channel (265) that houses a pair of resilient locking members (263). Integrated guidewire locking and rotation knob (264) may translate along resilient locking members (263). Further, channel (265) may be dimensioned to snap fit with resilient locking members (263) in order for resilient locking members (263) to lock against guidewire (266).

An inner lumen channel (278) extends from cantle (274), through integrated guidewire locking and rotation knob (264), through pommel (272), through a rapid exchange port (267) defined by dilation catheter (268), and to the open distal end of dilation catheter (268) past inflatable balloon (270). Inner lumen channel (278) is configured to receive guidewire (266). Additionally, guidewire (266) may be different dimensions. It should be understood from the foregoing that guidewire (266) and dilation catheter (268) may be secured together such that guidewire (266) and dilation catheter (268) translate unitarily together; yet guidewire (266) may still be rotated relative to dilation catheter (268).

It should also be understood from the foregoing that a user may insert a desired guidewire through inner lumen channel (278) until a distal end of guidewire extends out of the open distal end of dilation catheter (268) a desired length, and lock guidewire (266) in position via interaction between resilient locking members (263) and integrated guidewire locking and rotation knob (264). In other words, the user may selectively adjust the length of guidewire (266) that protrudes distally from the distal end of dilation catheter (268), then actuate locking members (263) to lock against guidewire (266) to secure the longitudinal position of guidewire (266) relative to dilation catheter (268). The selection of the length of guidewire (266) that protrudes distally from the distal end of dilation catheter (268) may be based on the targeted anatomical structure and/or other considerations. It should be understood that the selection of the distally protruding length of guidewire (266), and the longitudinal fixation of guidewire (266) relative to dilation catheter (268), may be performed before the medical procedure begins. It should also be understood that, in some versions, the length of guidewire (266) that protrudes distally from the distal end of dilation catheter (268) may be adjusted during a medical procedure (e.g., when the procedure moves from one anatomical structure to another anatomical structure).

Dilation catheter (268) of the present example further includes an outer lumen channel (280) in fluid communication with inflatable port (271) and inflatable balloon (270). Therefore, dilation catheter (268) may also inflate inflatable balloon (270). It should be understood that outer lumen channel (280) may be similar to inflation lumen (143) or first inner lumen described above. Outer lumen channel (280) may be fluidly isolated from rapid exchange port (267) and inner lumen (278).

It should also be understood that since unitary movement assembly (262) is capable of translating both guidewire (266) and dilation catheter (268) unitarily, integrated guidewire locking and rotation knob (264) may be longer than previous integrated guidewire locking and rotation knob (234) described above. Therefore, the length of knob (264) may be longer than width of the finger of a user. Other suitable variations will be apparent to those of ordinary skill in the art in view of the teachings herein.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A dilation catheter system, comprising: (a) a body, wherein the body comprises a distal end and a proximal end; (b) a shaft assembly extending past the distal end of the body, wherein the shaft assembly comprises: (i) a fixed guide member, wherein the fixed guide member is fixed relative to the body, (ii) a catheter shaft, (iii) a dilator fixed to the catheter shaft, wherein the catheter shaft is operable to expand the dilator, (iv) a removable guide member, wherein the removable guide member is operable to selectively attach to the body, wherein the catheter shaft is slidably disposed along the removable guide member such that the catheter shaft is configured to translate along the removable guide member, and (v) a guidewire slidably disposed within the removable guide member.

Example 2

The dilation catheter system of Example 1, wherein the dilation catheter system further comprises a dilation catheter grip slidably coupled to the body, wherein the dilation catheter grip is fixed to the catheter shaft, wherein the dilation catheter grip is configured to translate the catheter shaft relative to the body.

Example 3

The dilation catheter system of Example 2, wherein the dilation catheter system further comprises an inflation shaft, wherein the inflation shaft is in fluid communication with the catheter shaft and the dilator, wherein the inflation shaft is fixed relative to the catheter shaft such that the inflation shaft is translatable with the catheter shaft relative to the body.

Example 4

The dilation catheter system of any one or more of Examples 2 through 3, wherein the dilation catheter grip comprises an elongate body fixed to the catheter shaft.

Example 5

The dilation catheter system of any one or more of Examples 1 through 4, wherein the dilation catheter system further comprises a guidewire movement assembly slidably coupled to the body, wherein the guidewire movement assembly further comprises a grip and a rotary member, wherein the grip rotatably houses the rotary member, wherein the guidewire movement assembly is configured to translate the guidewire relative to the body.

Example 6

The dilation catheter system of Example 5, wherein the guidewire movement assembly is operable to rotate the guidewire about a longitudinal axis defined by the guidewire.

Example 7

The dilation catheter system of Example 6, wherein the guidewire extends through the body along a straight line.

Example 8

The dilation catheter system of Example 6, wherein the guidewire movement assembly further comprises a gearbox and a rotary shaft, wherein the rotary shaft is unitarily fixed to the rotary member, wherein the rotary shaft is configured to drive the gearbox, wherein the gearbox is configured to rotate the guidewire about the longitudinal axis defined by the guidewire.

Example 9

The dilation catheter system of Example 8, wherein the gearbox further comprises: (i) a first drive wheel unitarily fixed to the rotary member, (ii) a second drive wheel unitarily fixed to the guidewire, and (iii) a drive member associated with the first drive wheel and the second drive wheel, wherein the drive member is configured to rotate the second drive wheel in response to rotation of the first drive wheel.

Example 10

The dilation catheter system of any one or more of Examples 5 through 9, wherein the guidewire is fixed to the guidewire movement assembly via a shrink tubing attachment.

Example 11

The dilation catheter system of any one or more of Examples 1 through 10, wherein the dilation catheter system further comprises a guide member attachment assembly, wherein the guide member attachment assembly is configured to couple with the removable guide member in order to selectively fix the removable guide member relative to the body.

Example 12

The dilation catheter system of Example 11, wherein the guide member attachment assembly comprises a collet, wherein the collet is configured to actuate from an unlocked position to a locked position, wherein the collet is dimensioned to receive the removable guide member in the unlocked position, wherein the collet is configured to selectively fix the removable guide member relative to the body in the locked position

Example 13

The dilation catheter system of Example 12, wherein the removable guide member is configured to rotate and translate relative to the collet when the collet is in the unlocked position.

Example 14

The dilation catheter system of Example 12, wherein the guide member attachment assembly further comprises a static member, wherein the static member is fixed relative to the body, wherein the static body is dimensioned to house the collet.

Example 15

The dilation catheter system of Example 14, wherein the guide member attachment assembly further comprises a locking member, wherein the locking member is configured to actuate from a first position to a second position, wherein the collet is configured actuate from the unlocked position to the locked position in response to the locking member actuating from the first position to the second position.

Example 16

The dilation catheter system of Example 15, wherein the locking member is configured to rotate relative to the body in order to actuate from the first position to the second position.

Example 17

A dilation catheter system, wherein the dilation catheter system comprises: (a) a body; (b) a guide catheter extending from the body; (c) an actuating assembly configured to translate relative to the body, wherein the actuating assembly comprises: (i) a grip slidably coupled with the body, (ii) a rotation knob rotatably coupled with the grip, (iii) a dilation catheter comprising a proximal end and an open distal end, wherein the dilation catheter is fixed to the grip, wherein the dilation catheter comprises an expandable dilator, wherein the dilation catheter defines a rapid exchange port, (iv) an inner lumen channel extending from the grip through the rotation knob, through the rapid exchange port, and to the open distal end, and (v) a guidewire extending through the rapid exchange port out the open distal end of the dilation catheter.

Example 18

The dilation catheter system of Example 17, wherein the dilation catheter extends within the guide catheter, wherein the actuating assembly is configured to translate the dilation catheter past the guide catheter.

Example 19

The dilation catheter system of any one or more of Examples 17 through 18, wherein the rotation knob is configured to selectively fix to the guidewire.

Example 20

The dilation catheter system of Example 19, wherein the rotation knob is configured to rotate the guidewire relative to the dilation catheter.

Example 21

A dilation catheter system comprising: (a) a body; (b) shaft assembly extending from the body, wherein the shaft assembly comprises: (i) a catheter shaft, wherein the catheter shaft is configured to translate relative to the body, (ii) a dilator fixed to the catheter shaft, wherein the catheter shaft is configured to expand the dilator, and (iii) a removable guide member housed within the catheter shaft, wherein the catheter shaft is configured to translate along the removable guide member; and (c) a guide member attachment assembly, wherein the guide member attachment assembly is configured to selectively fix the removable guide member relative to the body.

Example 22

The dilation catheter system of any one or more of Examples 5 through 7, wherein the guidewire movement assembly further comprises a primary gear fixed to the rotary member, a secondary gear unitarily coupled to the guidewire, and an idler gear located between the primary gear and the secondary gear.

IV. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. A dilation catheter system, comprising:
(a) a body, wherein the body comprises a distal end and a proximal end; and
(b) a shaft assembly extending past the distal end of the body, wherein the shaft assembly comprises:
  (i) a fixed guide member comprising a distal portion and a proximal portion, wherein the fixed guide member is fixed relative to the body, wherein the proximal portion of the fixed guide member is configured to be disposed within the body and the distal portion of the fixed guide member extends past the distal end of the body,
  (ii) a catheter shaft,
  (iii) a dilator fixed to the catheter shaft, wherein the catheter shaft is operable to expand the dilator,
  (iv) a removable guide member configured to be disposed within the fixed guide member, wherein the removable guide member is operable to selectively attach to the body, wherein the catheter shaft is slidably disposed along the removable guide member such that the catheter shaft is configured to translate along the removable guide member, and
  (v) a guidewire slidably disposed within the removable guide member.

2. The dilation catheter system of claim 1, wherein the dilation catheter system further comprises a dilation catheter grip slidably disposed on the body, wherein the dilation catheter grip is fixed to the catheter shaft, wherein the dilation catheter grip is configured to translate the catheter shaft relative to the body.

3. The dilation catheter system of claim 2, wherein the dilation catheter system further comprises an inflation shaft, wherein the inflation shaft is in fluid communication with the catheter shaft and the dilator, wherein the inflation shaft is fixed relative to the catheter shaft such that the inflation shaft is translatable with the catheter shaft relative to the body.

4. The dilation catheter system of claim 2, wherein the dilation catheter grip comprises an elongate body fixed to the catheter shaft.

5. The dilation catheter system of claim 1, wherein the dilation catheter system further comprises a guidewire movement assembly slidably coupled to the body, wherein the guidewire movement assembly further comprises a grip and a rotary member, wherein the grip rotatably houses the rotary member, wherein the guidewire movement assembly is configured to translate the guidewire relative to the body.

6. The dilation catheter system of claim 5, wherein the guidewire movement assembly is operable to rotate the guidewire about a longitudinal axis defined by the guidewire.

7. The dilation catheter system of claim 6, wherein the guidewire extends through the body along a straight line.

8. The dilation catheter system of claim 6, wherein the guidewire movement assembly further comprises a gearbox and a rotary shaft, wherein the rotary shaft is unitarily fixed to the rotary member, wherein the rotary shaft is configured to drive the gearbox, wherein the gearbox is configured to rotate the guidewire about the longitudinal axis defined by the guidewire.

9. The dilation catheter system of claim 8, wherein the gearbox further comprises:
(i) a first drive wheel unitarily fixed to the rotary member,
(ii) a second drive wheel unitarily fixed to the guidewire, and
(iii) a drive member associated with the first drive wheel and the second drive wheel, wherein the drive member is configured to rotate the second drive wheel in response to rotation of the first drive wheel.

10. The dilation catheter of claim 5, wherein the guidewire movement assembly further comprises a primary gear fixed to the rotary member, a secondary gear unitarily coupled to the guidewire, and an idler gear located between the primary gear and the secondary gear.

11. The dilation catheter of claim 1, wherein the dilation catheter system further comprises a guide member attachment assembly, wherein the guide member attachment assembly is configured to couple with the removable guide member in order to selectively fix the removable guide member relative to the body.

12. The dilation catheter of claim 11, wherein the guide member attachment assembly comprises a collet, wherein the collet is configured to actuate from an unlocked position to a locked position, wherein the collet is dimensioned to receive the removable guide member in the unlocked position, wherein the collet is configured to selectively fix the removable guide member relative to the body in the locked position.

13. The dilation catheter system of claim 12, wherein the removable guide member is configured to rotate and translate relative to the collet when the collet is in the unlocked position.

14. The dilation catheter system of claim 12, wherein the guide member attachment assembly further comprises a static member, wherein the static member is fixed relative to the body, wherein the static member is dimensioned to house the collet.

15. The dilation catheter system of claim 14, wherein the guide member attachment assembly further comprises a locking member, wherein the locking member is configured to actuate from a first position to a second position, wherein the collet is configured actuate from the unlocked position to the locked position in response to the locking member actuating from the first position to the second position.

16. The dilation catheter system of claim 15, wherein the locking member is configured to rotate relative to the body in order to actuate from the first position to the second position.

17. A dilation catheter system, wherein the dilation catheter system comprises:
(a) a body;
(b) a guide catheter extending from the body; and
(c) an actuating assembly configured to translate relative to the body, wherein the actuating assembly comprises:
(i) a grip slidably coupled with the body,
(ii) a rotation knob rotatably coupled with the grip,
(iii) a dilation catheter comprising a proximal end and an open distal end, wherein the dilation catheter is fixed to the grip, wherein the dilation catheter comprises an expandable dilator, wherein the dilation catheter defines a rapid exchange port,
(iv) an inner lumen channel extending from the grip through the rotation knob, through the rapid exchange port, and to the open distal end,
(v) a guidewire extending through the rapid exchange port out the open distal end of the dilation catheter, and
(vi) a pair of locking members positioned in the inner lumen channel extending through the rotation knob configured to lock against the guidewire.

18. The dilation catheter system of claim 17, wherein the dilation catheter extends within the guide catheter, wherein the actuating assembly is configured to translate the dilation catheter past the guide catheter.

19. The dilation catheter system of claim 17, wherein the rotation knob is configured to selectively fix to the guidewire.

20. A dilation catheter system comprising:
(a) a body;
(b) shaft assembly extending from the body, wherein the shaft assembly comprises:
(i) a catheter shaft, wherein the catheter shaft is configured to translate relative to the body,
(ii) a dilator fixed to the catheter shaft, wherein the catheter shaft is configured to expand the dilator, and
(iii) a removable guide member housed within the catheter shaft, wherein the removable guide member is substantially rigid; and
(c) a guide member attachment assembly, wherein the guide member attachment assembly comprises a rotational arm configured to be operated by a user, wherein the rotational arm is configured to selectively fix the removable guide member relative to the body, wherein the catheter shaft is configured to translate along the removable guide member with the removable guide member fixed relative to the body.

* * * * *